US009566705B2

(12) United States Patent
Goldfarb et al.

(10) Patent No.: US 9,566,705 B2
(45) Date of Patent: Feb. 14, 2017

(54) MOVEMENT ASSISTANCE DEVICE

(71) Applicant: VANDERBILT UNIVERSITY, Nashville, TN (US)

(72) Inventors: Michael Goldfarb, Franklin, TN (US); Spencer Murray, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/408,094

(22) PCT Filed: Jun. 17, 2013

(86) PCT No.: PCT/US2013/046107
§ 371 (c)(1),
(2) Date: Dec. 15, 2014

(87) PCT Pub. No.: WO2013/188868
PCT Pub. Date: Dec. 19, 2013

(65) Prior Publication Data
US 2015/0142130 A1 May 21, 2015

Related U.S. Application Data

(60) Provisional application No. 61/660,286, filed on Jun. 15, 2012.

(51) Int. Cl.
*A61H 3/00* (2006.01)
*B25J 9/00* (2006.01)
(Continued)

(52) U.S. Cl.
CPC .............. *B25J 9/0006* (2013.01); *A61F 2/72* (2013.01); *A61H 1/024* (2013.01); *A61H 1/0244* (2013.01);
(Continued)

(58) Field of Classification Search
CPC ........ A61H 1/024; A61H 1/0244; A61H 3/00; A61H 2201/1215; A61H 2201/163; A61H 2201/1642; A61H 2201/5002; A61H 2201/5007; A61H 2201/5061; A61H 2201/5069; A61H 2201/1676; A61F 2/72; B25J 9/0006; Y10S 901/28
(Continued)

(56) References Cited

U.S. PATENT DOCUMENTS 5,101,472 A * 3/1992 Repperger ............... B25J 9/163
700/261
5,282,460 A * 2/1994 Boldt ........................ A61F 2/68
403/119
(Continued)

FOREIGN PATENT DOCUMENTS

| JP | 2003220584 | 8/2003 |
| JP | 2006075456 | 3/2006 |

OTHER PUBLICATIONS

Veneman et al.; "Design and Evaluation of the LOPES Exoskeleton Robot for Interactive Gait Rehabilitation"; IEEE Transactions on Neural Systems and Rehabilitation Engineering; vol. 15; Issue 3; 2007; pp. 379-386.*
(Continued)

*Primary Examiner* — Stephen Holwerda
(74) *Attorney, Agent, or Firm* — Nixon Peabody LLP

(57) ABSTRACT

An exoskeleton for applying force to at least one lower limb of a user includes a control system with a sensor interface for sensor signals; a power interface for transmitting control signals to the powered joint; a processor coupled to the sensor and the power interfaces; and a computer-readable medium storing a computer program executable on the processor with code sections for: estimating a configuration of a body of the user with respect to a gravity vector based on the sensor signals; computing a control torque for the
(Continued)

powered joint that compensates gravitational dynamics of the user based on the configuration; calculating a gravitational energy gradient for the powered joint; attenuating the control torque based on the gravitational energy gradient; computing a final control torque based on the attenuated control torque, and configuring the control signals based on the attenuated control torque.

19 Claims, 14 Drawing Sheets

(51) Int. Cl.
   A61H 1/02 (2006.01)
   A61F 2/72 (2006.01)
(52) U.S. Cl.
   CPC ......... *A61H 3/00* (2013.01); *A61H 2201/1215* (2013.01); *A61H 2201/163* (2013.01); *A61H 2201/1642* (2013.01); *A61H 2201/1676* (2013.01); *A61H 2201/5002* (2013.01); *A61H 2201/5007* (2013.01); *A61H 2201/5061* (2013.01); *A61H 2201/5069* (2013.01); *Y10S 901/28* (2013.01)
(58) Field of Classification Search
   USPC ............................... 623/25; 700/261; 901/28
   See application file for complete search history.

(56) References Cited

U.S. PATENT DOCUMENTS

| | | | | |
|---|---|---|---|---|
| 5,476,441 | A * | 12/1995 | Durfee | A61N 1/36003 434/112 |
| 7,190,141 | B1 * | 3/2007 | Ashrafiuon | B25J 9/0006 318/568.12 |
| 7,390,309 | B2 | 6/2008 | Dariush | |
| 2004/0249319 | A1 * | 12/2004 | Dariush | A61H 1/00 601/5 |
| 2008/0249438 | A1 * | 10/2008 | Agrawal | A61H 1/0237 601/35 |
| 2010/0256537 | A1 * | 10/2010 | Menga | B25J 9/0006 601/34 |
| 2010/0276944 | A1 | 11/2010 | Donelon et al. | |
| 2011/0166489 | A1 * | 7/2011 | Angold | A61H 1/0255 601/34 |
| 2011/0264015 | A1 * | 10/2011 | Endo | A61H 1/0255 601/35 |

OTHER PUBLICATIONS

Barak et al., "Issues in selecting outcome measures to assess functional recovery after stroke", NeuroRx (2006) 3(4): 505-524.
Barbeau et al., "Optimal outcomes obtained with body-weight support combined with treadmill training in stroke subjects", Arch Phys Med Rehabil (Oct. 2003) 84: 1458-1465.
Batchelor et al., "What works in falls prevention after stroke? A systematic review and meta-analysis", Stroke (2011) 41: 1715-1722.
Bogousslavsky et al., "The Lausanne Stroke Registry: Analysis of 1,000 consecutive patients with first stroke", Stroke (Sep. 1988) 19(9): 1083-1092.
Duncan et al., "Body-weight—Supported treadmill rehabilitation after stroke", New Engl J Med (May 26, 2011) 364(21): 2026-2036.
Duncan et al., "Protocol from the Locomotor Experience Applied Post-Stroke (LEAPS—trial: A randomized control trial", BMC Neurology (2007) 7: 39. (23 pages).
Farris et al., "Preliminary evaluation of a powered lower limb orthosis to aid walking in paraplegic individuals", IEEE Transactions on Neural Systems and Rehabilitation Engineering (Dec. 2011) 19(6): 652-659.
Forster et al., "Incidence and consequences of falls due to stroke: A systematic inquiry", BMJ (Jul. 8, 1995) 311: 83-86.
Hajek et al., "Cognitive and functional assessments of stroke patients: An analysis of their relation", Arch Phys Med Rehabil (Dec. 1997) 78: 1331-1337.
Harris et al., "Relationship of balance and mobility to fall incidence in people with chronic stroke", Physical Therapy (2005) 85: 150-158.
Hidler et al., "Alterations in muscle activation patterns during robotic-assisted walking", Clinical Biomechanics (2005) 20: 184-193.
Hidler et al., "Multicenter randomized clinical trial evaluating the effectiveness of the Lokomat in subacute stroke", Neurorehabil Neural Repair (2009) 23: 5-13.
Hsu et al., "Analysis of impairment influencing gait velocity and asymmetry of Hemiplegic patients after mild to moderate stroke", Arch Phys Med Rehabil (Aug. 2003) 84: 1185-1193.
Husemann et al., "Effects of locomotion training with assistance of a robot-driven gait othosis in hemiparetic patients after stroke: A randomized controlled pulot study", Stroke (2007) 38: 349-354.
Jorgensen et al., "Recovery of walking function in stroke patients: The Copenhagen Stroke Study", Arch Phys Med Rehabil (Jan. 1995) 76: 27-32.
Kelly-Hayes et al., "The influence of gender and age on disability following ischemic stroke: The Framingham Study", Journal of Stroke and Cerebrovascular Diseases (2003) 12(May 3-Jun.): 119-126.
Kidd et al., "The natural history and clinical consequences of aspiration in acute stroke", Q J Med (1995) 88: 409-413.
Mackintosh et al., "Falls and injury prevention should be part of every stroke rehabilitation plan", Clinical Rehabilitation (2005) 19: 441-451.
Macko et al., "Treadmill exercise rehabilitation improves ambulatory function and cardiovascular fitness in patients with chronic stroke: A randomized, controlled trial", Stroke (Oct. 2005) 36: 2206-2211.
Marchal-Crespo et al., "Review of control strategies for robotic movement training after neurologic injury", Journal of NeuroEngineering and Rehabilitation (2009) 6: 20. (15 pages).
Michael et al., "Reduced ambulatory activity after stroke: The role of balance, gait, and cardiovascular fitness", Arch Phys Med Rehabil (Aug. 2005) 86: 1552-1556.
Moseley et al., "Treadmill training and body weight support for walking after stroke", Stroke (2003) 34: 3006.
Neckel et al., "Abnormal joint torque patterns exhibited by chronic stroke subjects while walking with a prescribed physiological gait pattern", Journal of NeuroEngineering and Rehabilitation (2008) 5: 19-31.
Ottenbacher et al., "The reliability of the functional independence measure: A quantitative review", Arch Phys Med Rehabil (Dec. 1996) 77: 1226-1232.
Pohl et al., "Speed-dependent treadmill training in ambulatory hemiparetic stroke patients", Stroke (2002) 33: 553-558.
Pouwels et al., "Risk of hip/femur fracture after stroke: A population-based case-control study", Stroke (Oct. 2009) 40: 3281-3285.
Quintero et al., "A powered lower limb orthosis for providing legged mobility in paraplegic individuals", Top Spinal Cord Inj Rehabil (2011) 17(1): 25-33.
Quintero et al., "Control and implementation of a powered lower limb orthosis to aid walking in paraplegic individuals", IEEE Int Conf Rehabil Robot (2011). (19 pages).
Roger et al., "Heart disease and stroke statistics—2011 update: A report from the American Heart Association", Circulation (2011) 123: e18-e209.
Stineman et al., "The functional independence measure: Tests of scaling assumptions, structure, and reliability across 20 diverse impairment categories", Arch Phys Med Rehabil (Nov. 1996) 77: 1101-1108.
Sullivan et al., "Effects of task-specific locomotor and strength training in adults who were ambulatory after stroke: Results of the STEPS randomized clinical trial", Phys Ther (Dec. 2007) 87(12): 1580-1602.

(56) References Cited

OTHER PUBLICATIONS

Sullivan et al., "Step training with body weight support: Effect of treadmill speed and practice paradigms on postroke locomotor recovery", Arch Phys Med Rehabil (May 2002) 83: 683-691.
Weerdesteyn et al., "Falls in individuals with Stroke", JRRD (Nov. 8, 2008) 45: 1195-1214.
Werner et al., "Treadmill training with partial body weight support and an electromechanical gait trainer for restoration of gait in subacute stroke patients", Stroke (Dec. 2002) 33: 2895-2901.
Westlake et al., "Pilot study of Lokomat versus manual-assisted treadmill training for locomotor recovery post-stroke", Journal of NeuroEngineering and Rehabilitation (2009) 6: 18-29.

* cited by examiner

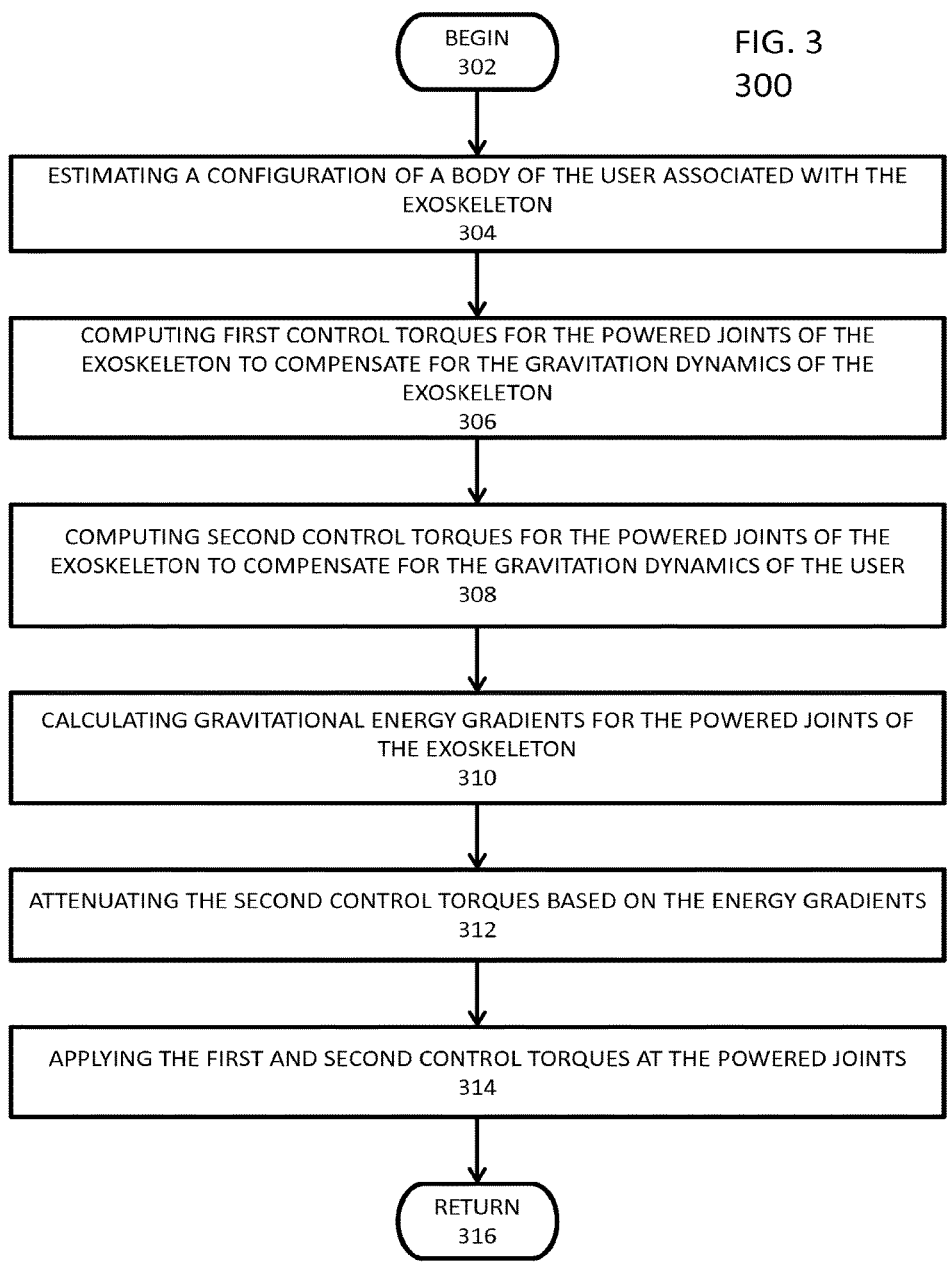

600

MOVEMENT ASSISTANCE DEVICE

CROSS-REFERENCE TO RELATED APPLICATIONS

This application is a §371 national stage entry of International Application No. PCT/US13/46107, filed Jun. 17, 2013, which claims priority to and the benefit of U.S. Provisional Patent Application No. 61/660,286, filed Jun. 15, 2012 and entitled "EXOSKELETON CONTROL METHOD", the contents of which herein incorporated by reference in their entirety.

FIELD OF THE INVENTION

The present invention relates to field of powered assistive devices, and more specifically to powered assistive devices and methods.

BACKGROUND

Approximately 800,000 people in the US suffer a stroke each year, of which approximately 660,000 (83%) survive. Of the surviving population, studies suggest approximately 60% (nearly 400,000) have lower extremity motor deficit in the acute stages of recovery. Of this population, studies suggest approximately half (i.e., 200,000) are unable to walk without assistance six months after the stroke. The inability to walk unassisted has an obvious impact on an individual's independence and community-dwelling capability, and thus quality of life. Similarly, impaired balance and compromised walking ability increase the incidence of falls and resulting fractures.

In an effort to improve mobility outcomes for the population of people with mobility deficit following stroke, body-weight-supported treadmill training (BWSTT) has been employed. In this intervention, a portion of a patient's body weight is suspended above a treadmill through an overhead suspension point, while one or more therapists manipulate portions of a patient's body, most commonly the lower limb, in order to emulate walking and thereby facilitate its recovery. A number of studies have been conducted investigating the efficacy of BWSTT for recovery after stroke, including. There is not general agreement in these studies regarding the efficacy of BWSTT, relative to conventional physical therapy interventions, although a number suggest that BWSTT provides no clear benefit relative to conventional therapy. In order to provide locomotor training similar to BWSTT with fewer therapists and perhaps greater consistency, robotic versions of BWSTT have been developed, which maintain the treadmill and overhead body weight suspension system, but replace the manual manipulation of the legs with robotic manipulation. Like manually-assisted (MA) BWSTT, robotic-assisted (RA) BWSTT systems have also been the subject of recent studies comparing their efficacy to conventional therapy. Like the MA-BWSTT studies, there is not general agreement regarding efficacy, although several studies suggest that the benefits of RA-BWSTT relative to conventional therapy are not clear.

BWSTT interventions offer little static or dynamic balance training. In the case of RA-BWSTT, the need for balance is nearly fully removed from the locomotion activity, while in the case of MA-BWSTT, the need for balance is largely absent. In both cases, overhead body-weight support is a substantially stabilizing effect, and in the specific case of the RA-BWSTT, trunk movement is kinematically constrained along a reduced set of movement axes. The presence of substantially stabilizing forces, in addition to kinematic constraints, significantly impedes the development of balance during such training.

The fact that balance is not required for BWSTT is in fact a substantial asset in early phases of therapeutic intervention for gait retraining. Most people in the rehabilitation community agree that early intervention can provide substantive therapeutic benefits, and many contend that BWSTT systems enable earlier therapeutic intervention than would otherwise be possible with conventional therapy. Despite this, as patients develop increased strength, the artificial stabilization present in the BWSTT interventions impedes the retraining of balance, which by necessity involves movement of the body in space, unimpeded movement of the trunk and upper and lower limbs, and proper placement of each foot to ensure dynamic stability. Integrating and coordinating these movements with the vestibular and proprioceptive systems, in accordance with the physics (i.e., dynamics) of locomotion, is a learned response that is essential to safe walking.

SUMMARY

Embodiments of the invention concern a control methodology, and devices therefrom, that assist a person by removing the energetic burdens of movement imposed by passive dynamics. The control methodology method preferably does not attempt to encourage or provide any movement. Rather, the control methodology preferably is configured to actively compensate for passive effects that must be overcome by a user in order to move. Specifically, these passive effects include, but are not limited to, forces required to move a body or load through gravity, and inertial forces required to accelerate or decelerate parts of a user's body, or load being carried. Other passive effects can include damping and/or stiffness in a user's joints (for example, due to contractures). A passive effect is defined as follows: for a system starting at an arbitrary configuration, moving through an arbitrary configuration, and returning to the original configuration, a passive effect will not perform any positive net work on the system. For example, for a mass that starts at a given point in space, is moved through a gravitational field, then returned to the original point of origin, the gravitational field will have performed zero net work on the mass, and thus the gravitational effect is regarded by the system as a passive effect. Since the net work performed on the system is zero in this case, the force field is considered a conservative field. If an object were moved through a damping field and returned to the starting point, the damping would have performed negative work on the system, and would also be considered a passive effect (in this case, since the net work performed on the system is negative, this force field is considered strictly passive). In the case that a system is returned to an original configuration and positive net work has been performed on the system, the effect would be considered active (or non-passive).

In a preferred embodiment, the control methodology exclusively attempts to remove passive barriers to movement, rather than otherwise supplement movement intent. With this control methodology, the exoskeleton preferably only responds to movement, but cannot cause it. Thus, the control methodology described herein enables the exoskeleton to contribute power to movement, without ever causing movement. As such, a substantial benefit of the proposed approach is that the exoskeleton can, in a preferred embodiment, avoid overriding a user's movement intent.

The control methodology can be used to variably or selectively remove passive burdens. For example, for a user who has a movement deficit, but still has partial strength, the approach can be used to remove a fraction of a set of passive effects (e.g., can remove half of the gravitational load, rather than the full load). The amount of passive compensation can adapt to the user, based on measured information, such a gait patterns.

In the case of a conservative force field (such as that imposed by gravity), ascending the gradient of the field requires work (i.e., power generation) on the part of the system, while descending the gradient of the field returns this work to the system. In the case of the exoskeleton, rather than compensating at all times for the conservative force fields, the control method can selectively compensate during the power generation portions of the movement (i.e., compensate only while ascending the gradient of the field). In this manner, the exoskeleton removes the burden of power generation from the user, but allows the user to benefit from the portions of movement which are aided by the conservative fields. Since the body in general contains multiple segments, and the direction of energy gradient for different segments may vary, the preferred embodiment for the control approach is to determine the joint-level energy gradient, using the sign and potentially magnitude of the product of the joint control torque and joint angular velocity to determine whether the gradient is positive or negative. In the case that the joint-level energy gradient is positive (i.e., the joint is working against gravity), the system can provide some degree of gravity compensation at the joint. In the case that the joint-level energy gradient is negative (i.e., the joint is working with gravity), the system need not provide gravity compensation. In some embodiments, when moving with the energy gradient (i.e., with gravity), the exoskeleton may provide a prescribed amount of joint-level damping.

In a first embodiment, there is provided a method for the control of an exoskeleton including at least one powered joint associated with lower limbs of a user. The method includes estimating a configuration of a body of the user associated with the exoskeleton with respect to a gravity vector and computing a first control torque for the at least one powered joint that at least partially compensates gravitational dynamics of the user based on the configuration. The method also includes calculating a gravitational energy gradient for the at least one powered joint, attenuating the first control torque based at least on the gravitational energy gradient to yield a second control torque, and applying a final control torque at the at least one powered joint, the final control torque based, at least in part, on the second control torque.

The method can also include computing a third control torque for the at least one powered joint that substantially compensates the gravitational dynamics of the exoskeleton, where the final control torque is then a sum of the second control torque and the third control torque.

In the method, the calculating of the gravitational energy gradient at the at least one joint can include ascertaining a product of the first control torque and a measured joint angular velocity of the at least one powered joint.

In the method, the estimating of the configuration can include utilizing at least one of a gyroscope or an accelerometer to determine an orientation of different segments of the body. The estimating of the configuration can further include sensing joint angles of the exoskeleton.

The estimating of the configuration can further include determining whether the user is in a single-support or a double-support phase. In response to determining that the lower limbs are in a single-support phase, the method can include computing the first control torque for a swing leg of the lower limbs to at least partially compensate for the weight of the swing leg relative to a hip of the user and computing the first control torque for a support leg of the lower limbs to at least partially compensate for the weight of the body. In response to determining that the lower limbs are in a double-support phase, the method can include computing the first control torque for the lower limbs to at least partially compensate for the weight of the body.

In the method, the first control torque can be selected to provide different amounts of partial gravity compensation for each of the lower limbs. Further, the first control torque for one of the lower limbs can be selected to be zero. Additionally, an amount of compensation provided by the first control torque can be selected to be different for each of the single-support phase and the double-support phase.

In the method, a transition of the lower limbs between the single-support phase and the double-support phase can be based on measurements from at least one of a load sensor, a gyroscope or an accelerometer. For example, the transition from the single-support phase and the double-support phase can be detected when the measurements indicate a substantial acceleration in the swing leg along the direction of ground impact. Also, the transition from the single-support phase and the double-support phase is detected when the measurement indicate a change in the direction of the angular velocity of the shank segment of the swing leg. Additionally, a transition of the lower limbs between the single-support phase and the double-support phase can be based on a change in at least one of the direction or the magnitude of the angular velocity of at least one segment of a swing leg.

In the method, an amount of compensation during the single-support phase can be determined based on a measured movement of the lower limbs. For example, the amount of compensation for a first leg of the lower limbs can be based, at least in part, on the measured movement of the second leg of the lower limbs. Also, the amount of compensation can based on the difference between the measured movement of the first leg and the measurement movement of the second leg.

The method can also include adjusting an amount of damping for the at least one powered joint.

In a second embodiment, a computer-readable medium having stored thereon a computer program executable on a computing device is provided. The computer program can include a plurality of code section for performing any of the methods described above with respect to the first embodiment.

In a third embodiment, a control system is provided for controlling an exoskeleton including at least one powered joint associated with lower limbs of a user and a plurality of sensors associated with the lower limbs. The control system includes a sensor interface for receiving sensor signals from the plurality of sensors, a power interface for transmitting control signals to the at least one powered joint, and a processor communicatively coupled to the sensor interface and the power interface. The control system also includes a computer-readable medium having stored thereon a computer program executable on the processor.

The computer program includes code sections for estimating a configuration of a body of the user associated with the exoskeleton with respect to a gravity vector based on the sensor signals at the sensor interface and computing a first control torque for the at least one powered joint that at least partially compensates gravitational dynamics of the user based on the configuration. The computer program also includes code sections for calculating a gravitational energy gradient for the at least one powered joint and attenuating the first control torque based at least on the gravitational energy gradient to yield a second control torque. Additionally, the computer program also includes code sections for computing a final control torque based, at least in part, on the second control torque and configuring the control signals at the power interface to cause the final control torque to be applied at the at least one powered joint.

The computer program can further include code sections for computing a third control torque for the at least one powered joint that substantially compensates the gravitational dynamics of the exoskeleton and the code sections for computing the final torque can include code sections for selecting a sum of the second control torque and the third control torque to be the final control torque.

Additionally, the computer program can include code sections for performing any of the methods described above with respect to the first embodiment.

BRIEF DESCRIPTION OF THE DRAWINGS

FIG. 3 is a flow chart of steps in an exemplary method for operating an exoskeleton in accordance with the various embodiments.

DETAILED DESCRIPTION

Figure 1:
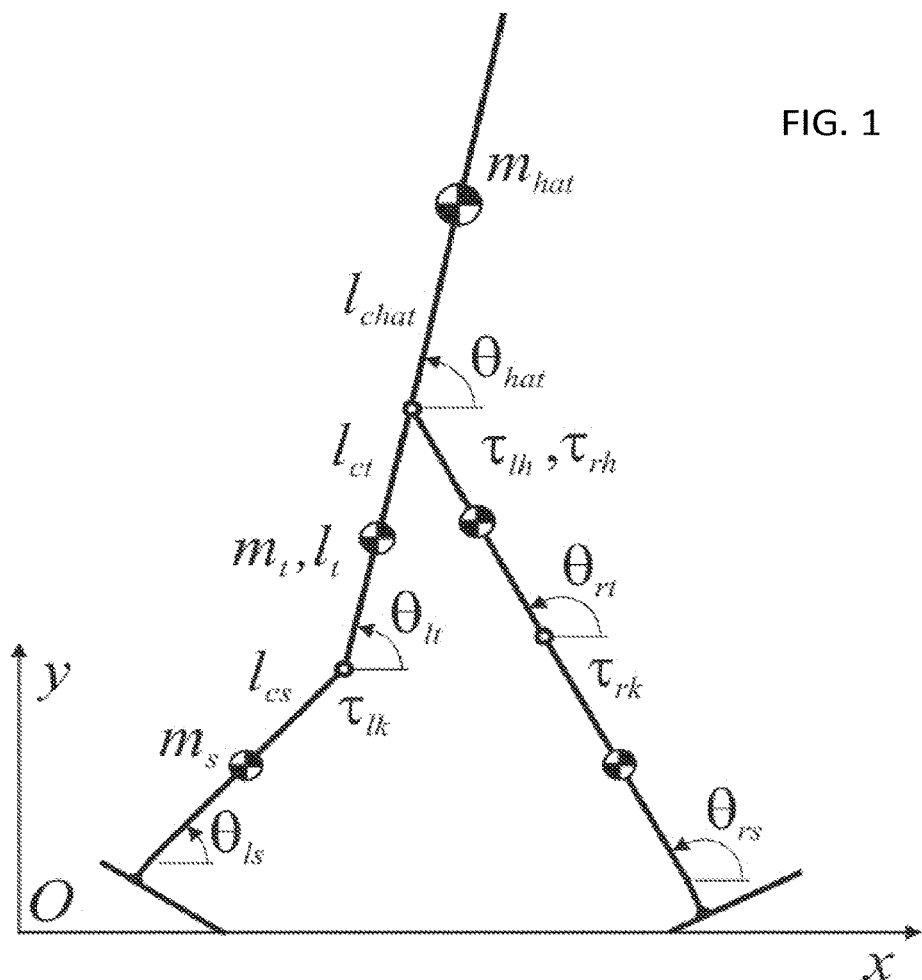
FIG. 1 illustrates schematically the variables and constants associated with locomotion.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, one of the limitations of existing post-stroke walking therapies is the lack of balance training. In view of these limitations, the present inventors propose a new control system and method for an exoskeletons consisting of a lower limb exoskeleton, and exoskeletons therefrom. The new control system and method facilitates overground locomotor training for persons with sub-acute stroke. Primarily, an exoskeleton configured in accordance with the various embodiments is intended for persons of sufficient strength and coordination to perform assisted walking, as characterized by a functional independence measure (FIM) gait score nominally in the range of three to five, although perhaps as low as two. Patients with lower FIM scores (e.g., one or two) may require, at least initially, other interventions, such as BWSTT or conventional therapy, until they have recovered sufficient strength and coordination to perform assisted walking using an exoskeleton in accordance with the various embodiments. Although the use of exoskeletons in accordance with the various embodiments will be described primarily with respect to standalone or isolated use, such device can also be used to supplement other therapies, and can help provide a continuum of care for persons in sub-acute stages of stroke recovery.

The terms "exoskeleton" or "exoskeleton system", as used herein, refers to any type of device that can be worn or otherwise attached to a user, where the device is configured to provide energy for motion of the one or more portions of the user.

The exoskeletons described here are primarily intended for use in a physical therapy gym under the supervision of a trained physical therapist. Further, these exoskeletons are also intended for use with a standard track-based (non-body-weight-support) overhead safety harness, the purpose of which is to prevent falling in the case of severe imbalance. Thus, like BWSTT interventions, the overground locomotor training will facilitate progressive development of strength and coordination. However, unlike BWSTT, the overground training using exoskeletons in accordance with the various embodiments requires dynamic balance, and therefore (along with the progressive development of strength) concomitantly facilitates the development of dynamic balance. Thus, in contrast to BWSTT, this use of exoskeletons in accordance with the various embodiments can build strength and coordination in the user, while also assisting the user to develop balance. These three elements are essential to safe walking.

Several major distinctions exist between the functionality of BWSTT, and that of the overground training facilitated by exoskeletons (i.e., exoskeleton-facilitated overground training or EFOT) in accordance with the various embodiments. These distinctions are enumerated as follows.

First, an exoskeleton in accordance with the various embodiments provides body weight support (BWS) from the ground up, rather than from an overhead suspension point. The former retains fully the dynamics associated with balance in overground locomotion, while the latter introduces a substantial, artificial stabilizing force that impedes the progressive development of balance during therapy.

Second, in addition to (fully or) partially compensating for the weight of the head, arms, and trunk (HAT) during stance phase, as is the norm in BWSTT, an exoskeleton in accordance with the various embodiments can be configured to additionally compensate for the distributed weight of the lower limb segments during both the swing and stance phases of gait (i.e., the BWS is distributed at the joint level). From a simplified perspective, the body weight support essentially offsets the gravitational load of the HAT during the stance phase of gait, and offsets the gravitational load of the swinging leg during the swing phase of gait. In some embodiments, body weight support can be separately provided for the HAT and each leg. Thus, rather than body weight support, the assistance provided by s exoskeleton in accordance with the various embodiments may be more accurately characterized as body segment weight compensation.

Third, since body weight support is provided by the exoskeleton from the ground up, the level of support can be different for affected and unaffected legs. One would assume for most individuals with hemiplegia that the unaffected leg would require substantially less body weight support than the affected leg.

Fourth, since the level of body weight support is individualized to each leg, and since the body weight support accounts for limb weight in addition to trunk weight, the level of body weight support can be further individualized within each phase of gait, such that the level of swing phase compensation can in general be different from the level of stance phase compensation. Note that stance phase largely requires use of extensor muscle groups in the lower limb, while swing phase largely requires use of flexor groups. Since the level of impairment between the two groups may be different, one can hypothesize that the ability to provide appropriate levels of assistance for each group will provide more effective progressive strengthening of the respective muscle synergies.

Fifth, since during some portions of the swing phase of walking gravity assists movement of the lower limb, the stance and swing legs can be compensated separately. In some embodiments, the swing limb compensation can be made active only during the portions of swing when the muscles are working against gravity. In this manner, the exoskeleton provides assistance to the muscle groups when working against gravity, but allows the gravitational field to offer full assistance when moving with gravity. Thus, the ballistic dynamics of swing phase are essentially preserved.

Sixth, unlike BWSTT systems, an exoskeleton in accordance with the various embodiments enables unrestricted movement through space (i.e., movement in sagittal, midsagittal, and frontal planes, and rotation within all planes). The coordination of sensory and motor systems required for balance in overground walking is clearly a three-dimensional task, and thus the development of such balance requires walking in space, not simply in a plane.

Seventh, the exoskeletons in accordance with the various embodiments make walking substantially easier (depending on the level of body segment weight compensation), without forcibly moving the patient's limbs. A benefit of this approach is that the patient cannot rely on the exoskeleton to initiate or provide movement (rather it only assists in movement generated by the patient). Thus, the issue of patient participation is made simpler, since the patient will not move without providing the effort to do so, and therefore the patient must be actively engaged in the therapy at all times (i.e., if they are not actively engaged, they won't move).

Eighth, like BWSTT, the level of assistance offered by exoskeletons in accordance with the various embodiments is (micro) computer-controlled, and therefore is easily changeable, and is expected to progressively decrease over the course of the therapeutic intervention, as the patient develops increased strength, coordination, and balance.

Ninth, unlike BWSTT, an exoskeleton in accordance with the various embodiments does not require the patient to walk at a constant rate (i.e., at a rate driven by a treadmill setting). Rather, walking rate is determined entirely by the patient, although target walking speeds can be encourage by the therapist as appropriate for the progressive recovery of function.

Finally, unlike BWSTT, an exoskeleton in accordance with the various embodiments can be used for therapies involving a number of different activities, including transitions from sitting to standing and standing to sitting. These activities are accommodated by the same body-segment-weight-compensation assistance approach used in the stance phase of gait (i.e., partial compensation for the weight of the head, arms, and trunk). Other activities include ascending or descending slopes, curbs, or stairs. Note that the nature of assistance remains the same for all such activities, although the extent of stance versus swing phase assistance may be altered, depending on the activity.

Although assistive controllers have been described for robotic-assisted BWSTT, these control approaches need not consider the effects of correctional forces on a subject's balance. In the case of BWSTT, it is common for either physical therapists or robotic mechanisms to impose corrective or assistive forces on the legs of the patient. These forces, which are meant to encourage appropriate walking movement, are effectively disturbances or perturbations with respect to the patient's ability to maintain balance. Since BWSTT provides external means of stabilization, such perturbations are inconsequential. In the case of EFOT, however, any perturbation of sufficient magnitude to alter the trajectory of the leg is similarly able to cause imbalance. Recall that for maintaining stability during locomotion, the foot should be placed such that the zero moment point of the patient lie within the support polygon formed between the patient and ground. Thus, the development of balance largely involves placing each foot in the "right" place at the "right" time. Given the relative muscular weakness of patients in the sub-acute stages of stroke recovery, an exoskeleton should provide assistance to the patient (i.e., make it easier to walk), without interfering with movement intention. As such, the inventors have developed and constructed an exoskeleton controller that is able to provide substantial movement assistance without introducing balance perturbations. The control method enables the exoskeleton to contribute power to movement, without ever causing movement. As such, a substantial benefit of the proposed approach is that the exoskeleton can never override a user's movement intent, and thus cannot interfere with the patient's foot placement.

As recognized in BWSTT, the primary load imposed on the lower limb during walking (and slow walking in particular) is the gravitational load. This is essentially the supporting body weight during stance and lifting leg weight during swing. With appropriate inertial sensing, a controller in accordance with the various embodiments can selectively compensate for the loads imposed by gravity. This is a subtractive rather than proactive control approach. Specifically, the controller configures the exoskeleton to make movement easier (nearly effortless in the case of full gravity compensation) and not to generate movement or impede movement. As previously mentioned, in cases (such as swing phase) where gravity assists limb movement, the controller can be easily modified such that compensation is only provided during movements against the gravitational energy gradient.

Prior to discussing the operation of the controller, it will be useful to define mathematical and physical variable and constants that will be used to describe the operation of the controller in the discussion below. These variables and constants are shown in FIG. 1. FIG. 1 is a schematic illustration of the variables and constants associated with locomotion of a body. First, as shown in FIG. 1, the body includes a series of masses. These include a mass of the head, arms, and trunk ($m_{hat}$) and for each leg a mass of the thigh ($m_t$) and a mass of the shank and foot ($m_s$). For an individual, the leg masses can be assumed to be substantially the same. FIG. 1 also illustrates a series of lengths. These include a length of the upper body ($l_{chat}$) that comprises the head, arms, and trunk. These lengths also include a thigh length ($l_{et}$) and a shank length ($l_{es}$). Again, as with the masses of the thigh and shank, the lengths of the thigh and shank are assumed to be substantially the same for an individual. The variables in FIG. 1 first include segment angles with respect to a ground or gravity reference. These angles include an upper body angle ($\theta_{hat}$), a left thigh angle ($\theta_{lt}$), a right thigh angle ($\theta_{rt}$), a left shank angle ($\theta_{ls}$), and a right shank angle ($\theta_{rs}$). The variables further include a right hip torque ($\tau_{rh}$), a right knee torque ($\tau_{rk}$), a left hip torque ($\tau_{lh}$), and a left knee torque ($\tau_{lk}$)

Figure 2:
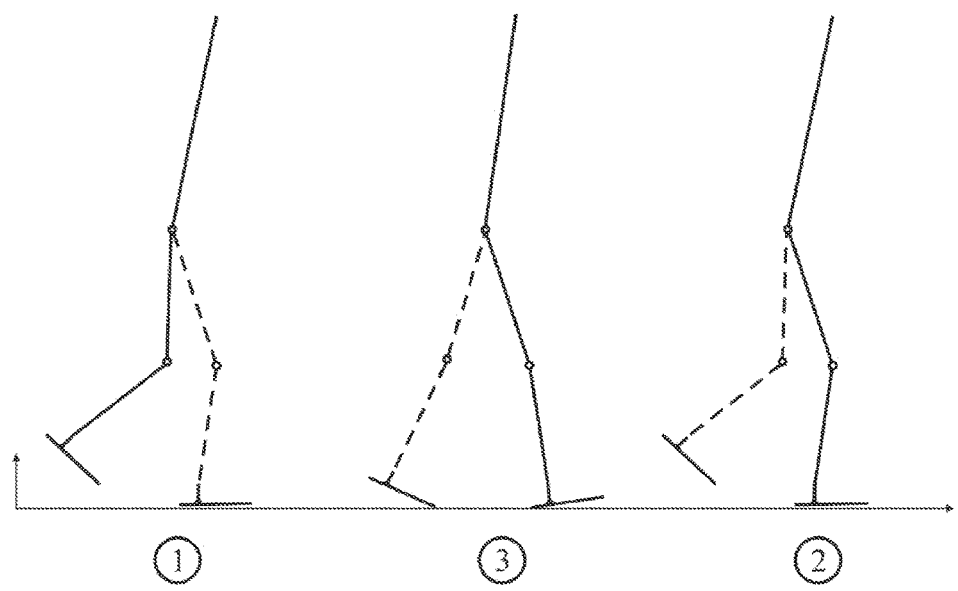
FIG. 2 illustrates schematically the different phases or states during walking.

The essence of the implementation of the controller is as follows. One can define the exoskeleton torque vector as:

$$\tau = [\tau_{rh} \tau_{rk} \tau_{lh} \tau_{lk}]^T \quad (1)$$

where the components represent the torques described above with respect to FIG. 1. There are three possible configurations of the exoskeleton, and three corresponding gravity compensation torque vectors. These are illustrated in FIG. 2. FIG. 2 is schematic illustration of basic walking configurations or states. As shown in FIG. 2, the first state (1) is when the left leg (shown as dotted line) is supporting the body (support leg) and the right leg (shown as solid line) is swinging (swing leg). The second state (2) is when the right leg (shown as solid line) is supporting the body (support leg) and the left leg (shown as dotted line) is swinging (swing leg). The third (3) state is when both the right leg (shown as solid line) and the left leg (shown as dotted line) are supporting the body.

Using the coordinate system and parameters defined in FIG. 1, the gravity compensation torque vector corresponding to state (1), single support with right leg in swing, is given by:

$$\tau_1 = g \begin{bmatrix} m_t l_{ct} \cos\theta_{rt} + m_s l_t \cos\theta_{rt} + m_s l_{cs} \cos\theta_{rs} \\ m_s l_{cs} \cos\theta_{rs} \\ m_{hat} l_{chat} \cos\theta_{hat} + m_t l_{ct} \cos\theta_{rt} + m_s l_t \cos\theta_{rt} + \\ m_s l_{cs} \cos\theta_{rs} \\ m_{hat} l_{chat} \cos\theta_{hat} + m_t l_{ct} \cos\theta_{rt} + m_s l_t \cos\theta_{rt} + \\ m_s l_{cs} \cos\theta_{rs} + (m_{hat} + m_t + m_s) l_s \cos\theta_{lt} + \\ m_t (l_t - l_{ct}) \cos\theta_{lt} \end{bmatrix}, \quad (2)$$

the gravity compensation torque vector corresponding to state (2), single support with left leg in swing, is given by:

$$\tau_2 = g \begin{bmatrix} m_{hat} l_{chat} \cos\theta_{hat} + m_t l_{ct} \cos\theta_{lt} + m_s l_t \cos\theta_{lt} + \\ m_s l_{cs} \cos\theta_{ls} \\ m_{hat} l_{chat} \cos\theta_{hat} + m_t l_{ct} \cos\theta_{lt} + m_s l_t \cos\theta_{lt} + \\ m_s l_{cs} \cos\theta_{ls} + (m_{hat} + m_t + m_s) l_s \cos\theta_{rt} + \\ m_t (l_t - l_{ct}) \cos\theta_{rt} \\ m_t l_{ct} \cos\theta_{rt} + m_s l_t \cos\theta_{rt} + m_s l_{cs} \cos\theta_{rs} \\ m_s l_{cs} \cos\theta_{ls} \end{bmatrix}, \quad (3)$$

and, assuming a symmetric distribution of joint torques in the double support phase, the gravity compensation torque vector corresponding to state 3, double support, is given by:

$$\tau_3 = g \begin{bmatrix} \frac{1}{2} m_{hat} l_{chat} \cos\theta_{hat} \\ \frac{1}{2} m_{hat} l_t \cos\theta_{rt} + m_t (l_t - l_{ct}) \cos\theta_{rt} + \frac{1}{2} m_{hat} l_{chat} \cos\theta_{hat} \\ \frac{1}{2} m_{hat} l_{chat} \cos\theta_{hat} \\ \frac{1}{2} m_{hat} l_t \cos\theta_{lt} + m_t (l_t - l_{ct}) \cos\theta_{lt} + \frac{1}{2} m_{hat} l_{chat} \cos\theta_{hat} \end{bmatrix}. \quad (4)$$

These torques can be used to determine how much torque needs to be applied at the hip and knee joints in order to compensate of the gravitational dynamics of the user. That is, to compensate for the forces of gravity operating against a user during walking.

It is worth noting that equations (2)-(4) provide values that correspond to full gravity compensation at the hip and knee joints of both legs. However, one objective of the proposed EFOT body-mass-compensation controller is partial body mass compensation. Another objective or option, is to provide different amounts of compensation for an affected leg and an unaffected leg. A third objective or option could also be to provide different amounts of compensation for a leg during stance and swing.

Accordingly, the various embodiments allow the controller to adjust torques to provide different type of gravity compensation. For example, in one embodiment, one could let $0 \le r_o < 1$ be the fraction of body mass compensation desired for and affected leg and $0 \le r_a < 1$ be the fraction of body mass compensation desired for the unaffected leg, where $r_a$ and $r_u$ can be the same or different. In operation, partial body mass compensation can then be provided by scaling each respective component of the compensation torque vector by the appropriate fraction. For example, the two torque components on the affected leg can be scaled by the fraction $r_a$ and the two torque components on the unaffected leg can be scaled by the fraction $r_u$. Note that the fraction can in general be different for each of the configuration states shown in FIG. 2.

As previously mentioned, in order to preserve a ballistic swing phase, one can provide gravity compensation only in the case the joint is working against gravity, which can be determined by the sign of each element of the inner product of the gravity compensation torque vector and the respective joint angular velocity vector. When the respective element is positive, the exoskeleton is performing work (movement is against the gravity field), and the gravity compensation component should be retained. When the respective element is negative, movement is with the gravitational field, and the gravity compensation component can be turned off, in order to facilitate the ballistic portions of swing phase. Finally, although not explicitly shown here, the exoskeleton also implements the full gravity compensation of its own segment masses. This compensation is structured in the same manner as equations (2)-(4), although it is not subject to scaling fractions or "ballistic" switching, since the objective of this component is simply to compensate as much as possible for the gravitational dynamics of the exoskeleton itself (i.e., to erase the weight of the exoskeleton, to the extent possible).

As described above, the control methodology of the various embodiments distinguishes between the swing phase and stance phase of gait, and can offer different types of gravity compensation during each phase. In particular, the control methodology can compensate (or partially compensate) for the weight of the swing leg relative to the hip during the swing phase of gait, while the control methodology compensates (fully or partially) for the weight of the stance leg, body, and swing leg relative to the ground during stance. In both cases, the extent of gravity compensation can vary depending on the direction of the energy gradient at each joint.

To operate in the manner described above, the control methodology must be able to distinguish between the stance and swing phases of gait for each leg. As such, the control methodology can be implemented in the form of a state controller, where the transition between swing and stance can be indicated by the occurrence of one or more events or the configuration of the exoskeleton meeting one or more pre-defined conditions. For example, a foot switch or load sensor can be provided in the exoskeleton, which indicates a transition when activated. In another example, the transition from swing to stance can be indicated by an accelerometer to detect the impact of heel strike on the respective leg via a substantial change in the acceleration of the leg. In yet another example, the termination of a swing phase can be determined based on a timer. In still another example, the transition from stance to swing can be indicated using a gyroscope to indicate a substantial change in the angular velocity of leg segments. In some embodiments, these sensor-based signals can be used in association with changes in the internal configuration of the exoskeleton, such as the knee angle, hip angle, or differential hip angle.

In additional to inter phase control, intra-phase control can be provided as well. That is, in some instances it can be useful to adjust the amount of compensation within a phase. For example, the extent of gravity compensation assistance can be partially or fully attenuated near the transitions between stance phase and swing phase. In another configuration, heel strike of the contralateral leg can indicate late stance, in which case gravity compensation can be phased out of the stance leg, until swing phase is detected.

FIG. 3 illustrates a flow chart of steps in an exemplary method 300 for controlling an exoskeleton in accordance with the various embodiments described above. Method 300 begins at step 302 and continues on to step 304. At step 304, an estimate of the configuration of the body of the user (and the exoskeleton) is obtained. For example, the values for the various constants and variables illustrated in FIG. 2 can be obtained. Some of these values, such as masses and lengths, can be predefined and stored in a computer memory device or the like. Other values, such as angles and torques, can be measured directly or indirectly. Additionally, this step can also involve monitoring other sensors (e.g., load sensors, gyroscopes, etc.) that would assist in ascertaining the configuration of the body.

Once the configuration of the body is obtained at step 304, the method 300 proceeds to steps 306 and 308 to compute control torques. At step 306, first control torques to for the powered joints to compensate for the gravitational dynamics of the exoskeleton are computed. These can be derived, as described above in a manner substantially similar to that described in equations (1)-(4) to obtain control torques for the powered joints that effectively cancel or compensate the load of the exoskeleton on the user. At step 308, second control torques are computed, as described above with respect to equations (1)-(4) to compensate (fully or partially) the gravitational dynamics of the user. That is, to compensate for the weight of the body or the weight of a leg in a swing phase to provide assistance to the user. Steps 306 and 308 can be performed sequentially or concurrently.

Once the second control torques at step 308 are obtained, the energy gradients are computed at step 310. For example, as described above, the product of a second control torque for a joint and the angular velocity of the joint can be obtained. Thereafter, at step 312, the second control torques obtained at step 308 are attenuated. This attenuation can involve a scaling of the second control torques, as discussed above, to adjust the amount of assistance for the user. This attenuation can also involve, for example, setting a second control torque for a particular joint to zero. For example, as described above, where the energy gradient is negative for a joint, the joint can be configured to provide reduced or zero assistive power. As noted above, the attenuation amount and type can vary depending on the configuration of the body, an activity type or phase, and from joint to joint.

Finally, once the second control torques are attenuated at step 312, the first control torques and the attenuated second control torques can be applied to the powered joints at step 314. The method 300 can then resume previous processing at step 316, including repeating method 300. It should be noted that method 300 can include additional steps or fewer steps than shown in FIG. 3. For example, method 300 can also include determining an activity or activity phase or damping of one or more of the powered joints. However, the various embodiments are not limited in this regard and any other steps can also be performed.

Although the various embodiments can be utilized with a number of exoskeletons, one exemplary exoskeleton is described below for purposes of illustration. However, the various embodiments are not limited to this particular configuration and the control methodology described herein can be utilized with any other exoskeleton systems.

Figure 4A:
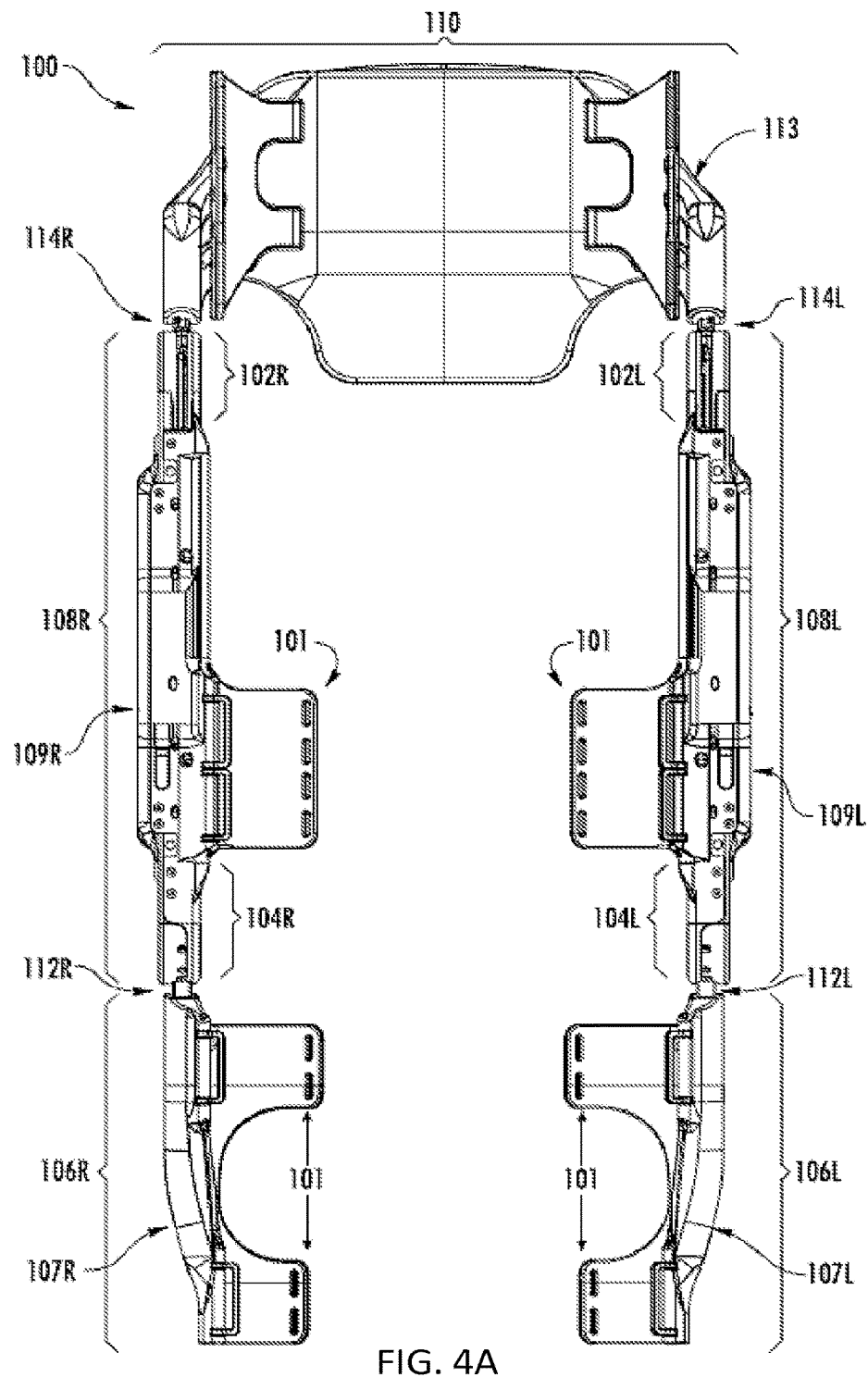
FIG. 4A shows a front view of an exoskeleton that can be used with the control methodology of the various embodiments.
Figure 4B:
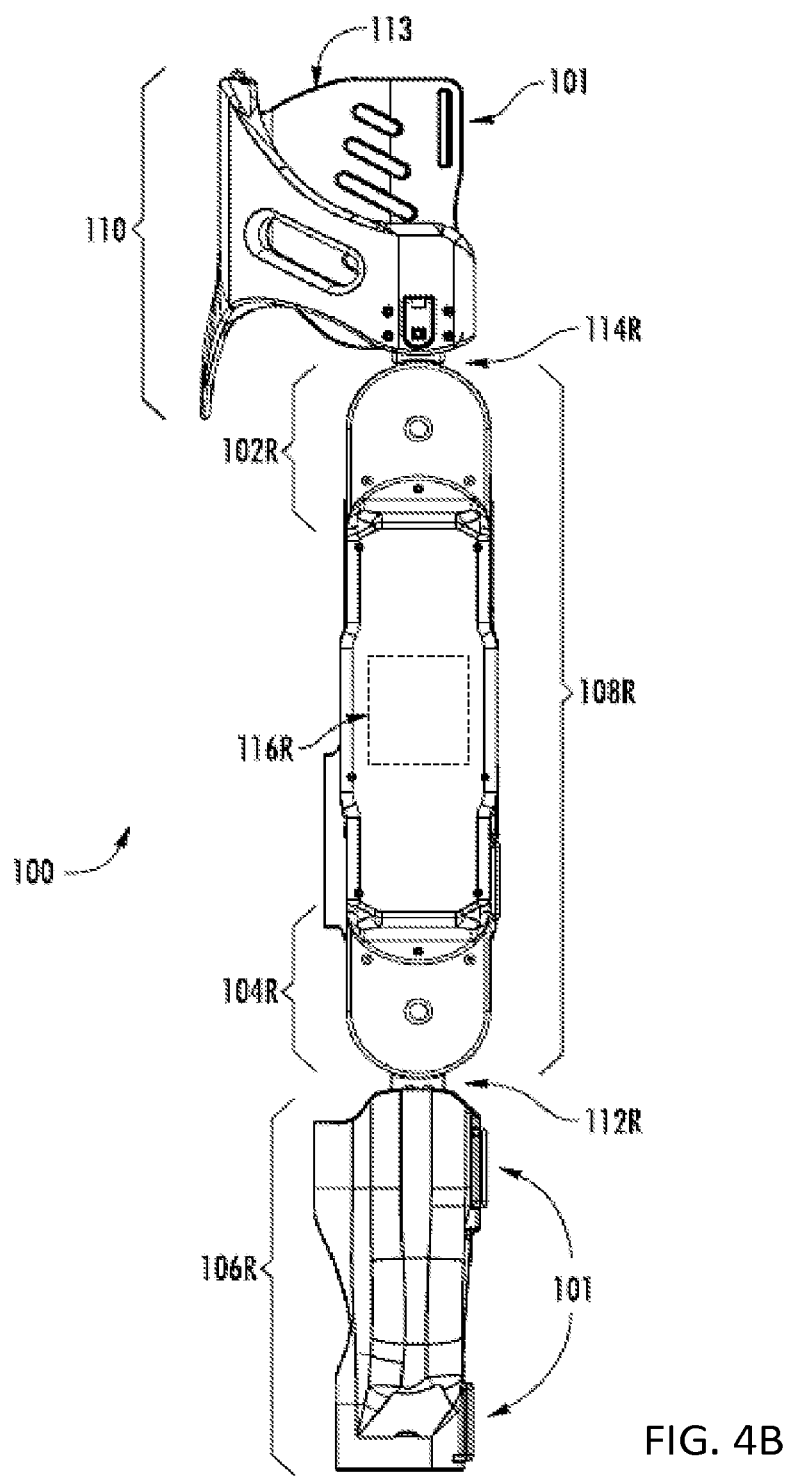
FIG. 4B shows a side view of the exoskeleton shown in FIG. 4A.
Figure 4C:
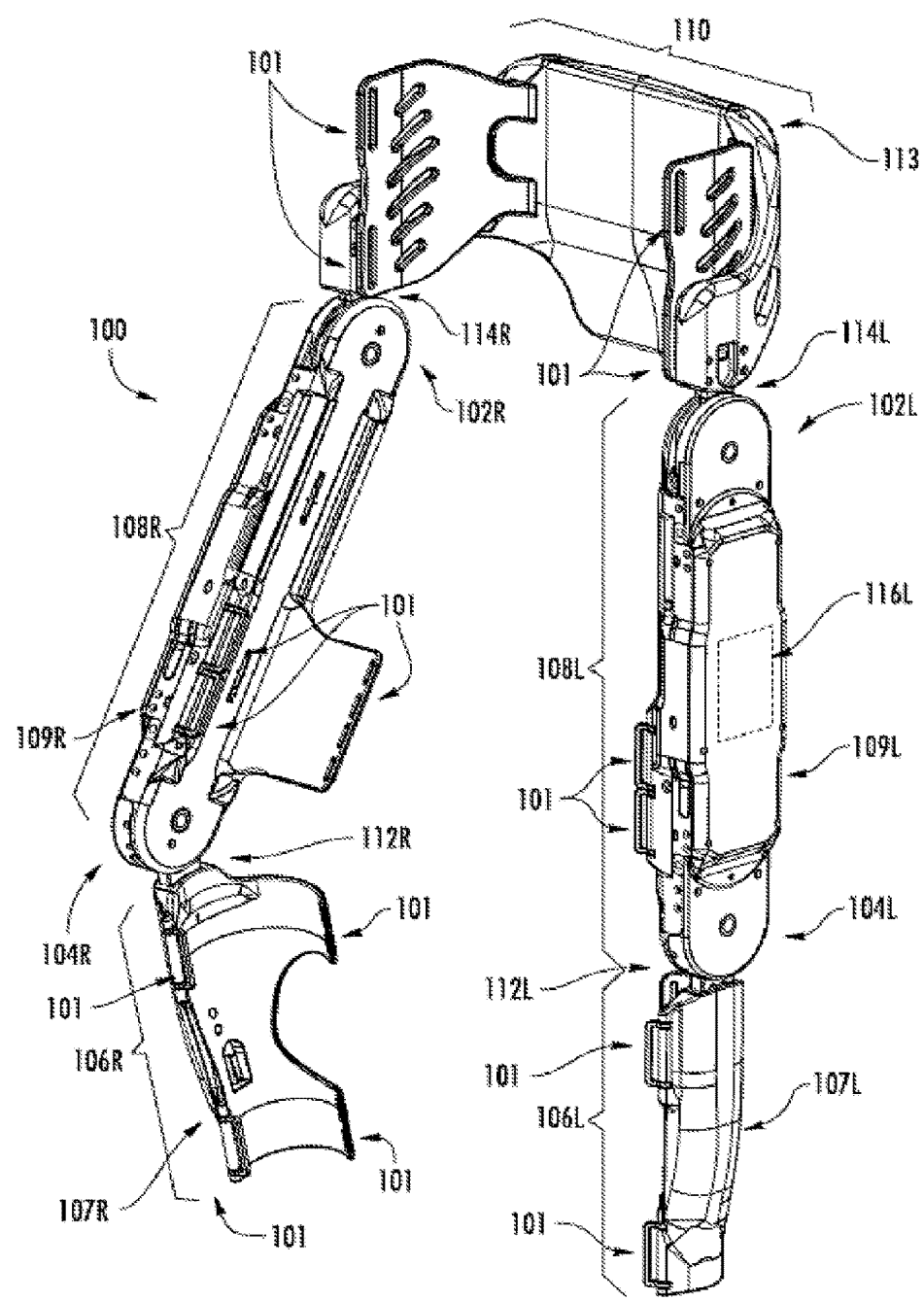
FIG. 4C shows an isometric view of the exoskeleton shown in FIG. 4A.
Figure 5A:
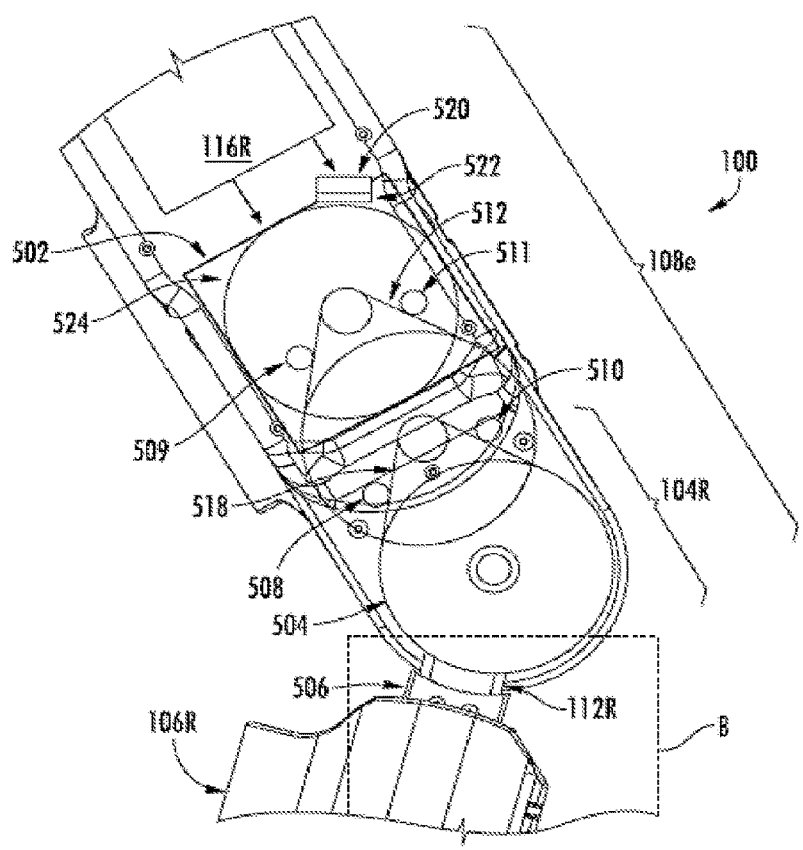
FIG. 5A shows a partial cutaway view of a portion of the exoskeleton shown in FIG. 4A.
Figure 5B:
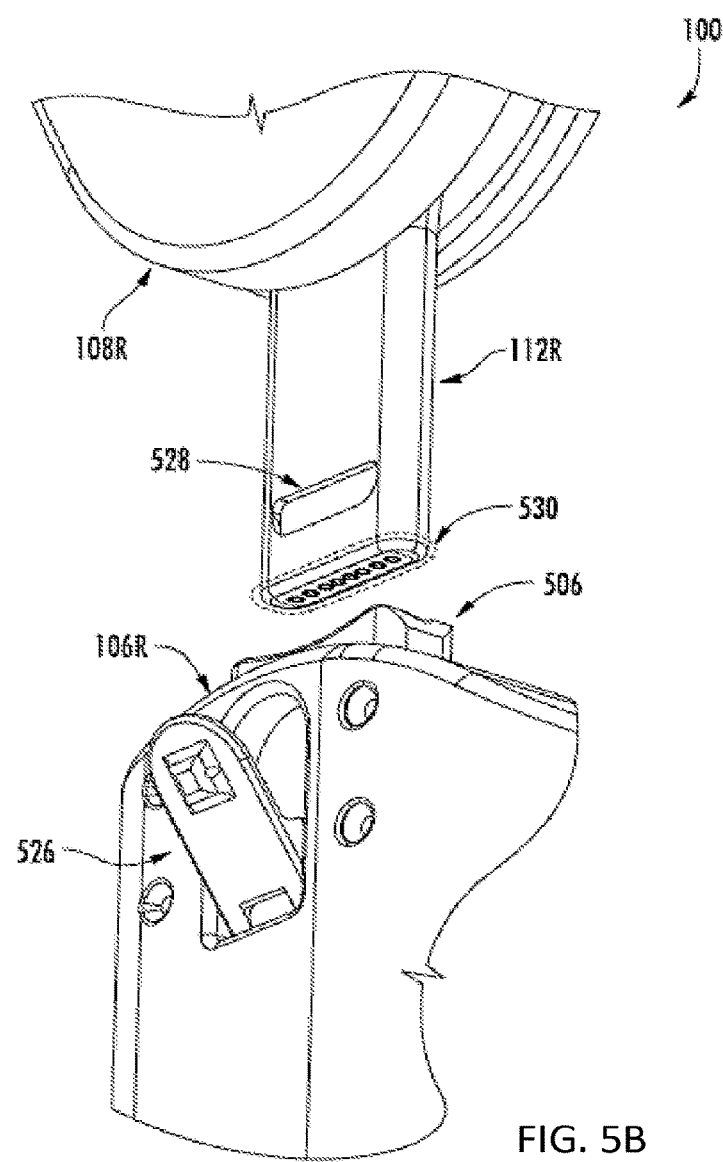
FIG. 5B is a detailed exploded view of section B of FIG. 5A.
Figure 6:
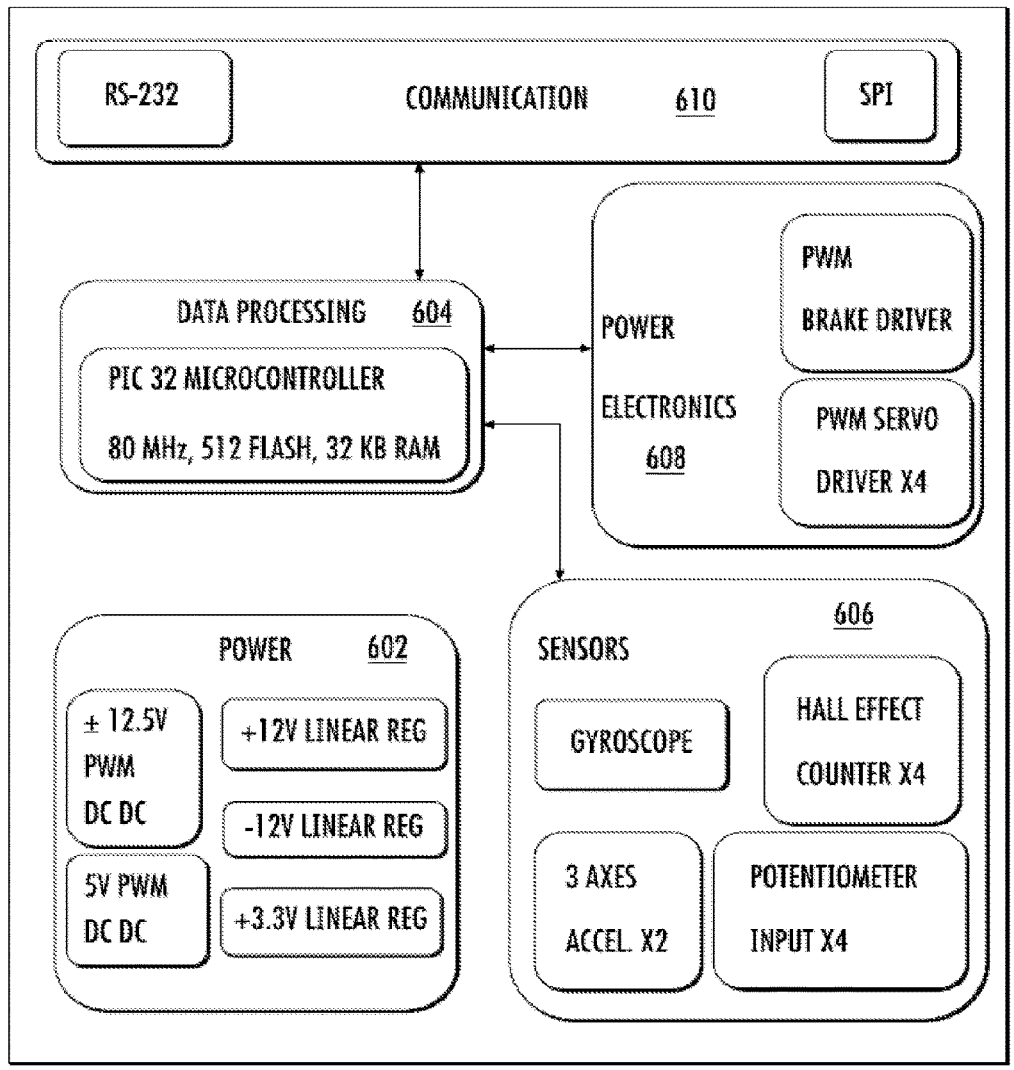
FIG. 6 is a functional diagram of an exemplary distributed embedded system for an exoskeleton in accordance with the various embodiments.

An exemplary powered lower limb exoskeleton 100 in accordance with the various embodiments is shown in FIGS. 4A, 4B, 4C, 5A, 5B, and 6. FIGS. 4A and 4B show front and side views, respectively, of the exoskeleton 100. FIG. 4C shows an isometric view of the exoskeleton 100. FIG. 5A shows a partial cutaway view of a portion of the exoskeleton 100. FIG. 5B is a detailed exploded view of section B of FIG. 5A. FIG. 6 is a functional diagram of an exemplary distributed embedded system for an exoskeleton in accordance with the various embodiments;

Specifically, the exoskeleton 100 shown in these figures incorporates four motors, which impose sagittal plane torques at each hip joint 102R, 102L and knee joint 104R, 104L. The exoskeleton 100 can be used with a stability aid 103, such as crutches, a walker, or the like.

As seen in the figures, the exoskeleton contains five segments, which are: two shank segments 106R and 106L, two thigh segments 108R and 108L, and one hip segment 110. Each of thigh segments 108R and 108L includes a thigh segment housing 109R and 109L, respectively, and link or connector 112R and 112L, respectively, extending from each of the knee joints 104R and 104L and configured for moving in accordance with the operation of the knee joints 104R and 104L to provide sagittal plane torque at the knee joints 104R and 104L. The connectors 112R and 112L are further configured for mechanically coupling each of thigh segments 108R and 108L to respective ones of the shank segments 106R and 106L. Further, each of thigh segments 108R and 108L also includes a link or connector 114R and 114L, respectively, extending from each of the hip joints 102R and 102L and moving accordance with the operation of the hip joints 102R and 102L to provide sagittal plane torque at the knee joints 104R and 104L. The connectors 114R and 114L are further configured for mechanically coupling each of thigh segments 108R and 108L to the hip segment 110.

The exoskeleton 100 can be worn by a user. To attach the exoskeleton to the user, the exoskeleton 100 can include fastening points 101 for attachment of the exoskeleton to the user via belts, loops, straps, or the like. Further, for comfort of the user, the exoskeleton 100 can include padding (not shown) disposed along any surface likely to come into contact with the user.

In some embodiments, the various components of exoskeleton 100 can be dimensioned for the user. However, in other embodiments, the component can be configured to accommodate a variety of users. For example, in some embodiments, one or more extension elements can be disposed between the shank segments 106R and 106L and the thigh segments 108R and 108L to accommodate users with longer limbs. In other configurations, the lengths of the two shank segments 106R and 106L, two thigh segments 108R and 108L, and one hip segment 110 can be adjustable. That is, thigh segment housings 109R, 109L, the shank segment housings 107R and 107L for the shank segments 106R, 106L, respectively, and the hip segment housing 113 for the hip segment 110 can be configured to allow the user or prosthestist to adjust the length of these components in the field. For example, these components can consist of slidable or movable sections that can be held in one or more positions using screws, clips, or any other types of fasteners. In view of the foregoing, the two shank segments 106R and 106L, two thigh segments 108R and 108L, and one hip segment 110 can form a modular system allowing for one or more of the components of the exoskeleton 100 to be selectively replaced and for allowing an exoskeleton to be created for a user without requiring customized components. Such modularity can also greatly facilitate the procedure for donning and doffing the device.

In exoskeleton 100, disposed within each of thigh segment housings 109R, 109L includes substantially all the components for operating corresponding ones of the knee joints 104R, 104L and the hip joints 102R, 102L. In particular, each of thigh segment housings 109R, 109L includes two motors which are used to drive the hip and knee articulations. However, the various embodiments are not limited in this regard and some components can be located in the hip segment 110 and/or the shank segments 106R, 106L. For example, a battery 111 for the exoskeleton can be located within in hip segment housing 113 and connectors 114R and 114L can also provide means for connecting the battery 111 to any components within either of thigh segments 108R and 108L. For example, the connectors 114R and 114L can include wires, contacts, or any other types of electrical elements for electrically connecting battery 111 to electrically powered components in thigh segments 108R and 108L. In the various embodiments, the placement of battery 111 is not limited to being within hip segment housing 113. Rather, the battery can be one or more batteries located within any of the segments of exoskeleton 100.

In the various embodiments, in order to maintain a low weight for exoskeleton and a reduced profile for the various components, a substantially planar drive system is used to drive the hip and knee articulations. For example, each motor can each drive an associated joint through a speed-reduction transmission using an arrangement of sprocket gears and chains substantially parallel to the plane of sagittal motion. One exemplary configuration for such an arrangement of a motor is illustrated in FIG. 5A. Using the configuration in FIG. 5A, it is possible to achieve a low profile exoskeleton, adding less than 5 cm at the hip and thigh sections.

For example, in one embodiment, the profile of the exoskeleton in the frontal plane can be configured so as to add 3.2 cm at the hip and knee joint, and 4.8 cm at mid-thigh, such that a user is able to sit in a conventional armchair or wheelchair. Similarly, the hip segment protrudes approximately 3.2 cm posteriorly from the user's lower back, such that it should not significantly interfere with a seat back. The exoskeleton does not extend above mid-abdomen and requires nothing to be worn over the shoulders and nothing above the lower back, which presumably renders the device less noticeable when sitting at a desk or table. The compact design of the exoskeleton is greatly facilitated by the integration of the distributed embedded system within the exoskeleton structure.

In the various embodiments, the exoskeleton 100 is not configured for weight bearing. That is, as shown in FIGS. 4A-4C, the exoskeleton 100 will not include feet or other weight bearing structures. Rather, as shown in FIG. 1, the exoskeleton 100 is configured so that the combined length of the shank segments 106R and 106L and the corresponding one of the thigh segments 108R and 108L is less than a length of the leg of the user. This results in an exoskeleton with potential health benefits for the user. In particular, the ability to stand and walk can reverse or reduce the amount of physiological impairments typically associated with immobility, including muscular atrophy, loss of bone mineral content, frequent skin breakdown problems, increased incidence of urinary tract infection, muscle spasticity, impaired lymphatic and vascular circulation, impaired digestive operation, and reduced respiratory and cardiovascular capacities.

Although FIG. 5A will be described with respect to the operation of knee joint 104R, this is for ease of illustration. That is, the other joints can be configured to operate in a substantially similar manner. FIG. 5A is a cutaway view of exoskeleton 100 around knee joint 104R illustrating one exemplary configuration for a motor 502 driving knee joint 102R in an exoskeleton in accordance with the various embodiments. As shown in FIG. 5A, the knee joint 102R can be implemented by disposing a joint sprocket gear 504 at one end of thigh segment housing 109R parallel to the sagittal plane and configuring the joint sprocket gear 504 to rotate parallel to the sagittal plane. To provide the sagittal plane torque for knee joint 102R, the connector 112R can extend from the joint sprocket gear 504 and be mechanically connected, so that rotation of the joint sprocket gear 504 results application of torque to the shank segment 106. As shown in FIG. 5A, a slot or receiving element 506 can be provided for the connector 112R to link the thigh segment 108R and shank segment 106R. The receiving element 506 and the connector 112R can be configured such that the connector can removably connect the thigh segment 108R and shank segment 106R. In the various embodiments, clips, screws, or any other types of fastener arrangements can be used to provide a permanent or a removable connection. In some embodiments, quick connect or "snap-in" devices can be provided for providing the connection. That is, these quick connect devices allow connections to be made without the need of tools. These types of quick connect devices can not only be used for mechanically coupling, but for electrical coupling. In some embodiments, a single quick connect device can be used to provide both electrical and mechanical coupling. However, the various embodiments are not limited in this regard and separate quick connect devices can be provided for the electrical and mechanical coupling. It is worth noting that with quick disconnect devices at each joint, the exoskeleton can be easily separated into three modular components—right leg, left leg, and hip segment—for ease of donning and doffing and also for increased portability.

A detailed view of an exemplary quick-connect configuration is shown in FIG. 5B. FIG. 5B is a detailed view of section "B" of FIG. 5A. As shown in FIG. 5B, the connector 112R is a member that extends from thigh segment 108R. The connector 112R is configured to slide into receiving element 506. The connector 112R can then be mechanically locked into place via the combination of a latch 526 on shank segment 106R and a catch 528 on connector 112R.

As noted above, the connectors 112R, 112L, 114R, and 114L can be configured to provide mechanical and electrical connections. Referring back to FIG. 5B, in the event that an electrical connection is needed between the thigh segment 108R and shank segment 106R, wires can be routed through the interior of connector 112R to electrical contacts 530. A corresponding set of electrical contacts (not shown) would also be provided in the interior of receiving element 506. Accordingly, when connector 112R is locked into receiving element 506, the electrical contacts 530 are placed in contact with the electrical contacts within receiving element 506. A similar configuration can be provided for links 112L, 114R, and 114L. It is noted though that the various embodiments are not limited to solely the catch and latch combination of FIG. 5B. Rather any other type of fastening or locking mechanism can be used without limitation.

Referring back to FIG. 5A, the knee joint 104R is actuated via operation of motor 502, as discussed above. The motor 502 can be an electric motor that drives the knee joint 104R (i.e., joint sprocket gear 504) using a two-stage chain drive transmission. For example, as shown in FIG. 5A, a first stage can consist of the motor 502 driving, either directly or via a first chain 512, a first drive sprocket gear 514. The first drive sprocket gear 514 is mechanically coupled to a second drive sprocket gear 516 so that they rotate together about the same axis based on the power applied by motor 502 to first drive sprocket gear 514. The second drive sprocket gear 516 can be arranged so that it is disposed in the same plane as the joint gear 504. Thus, a second chain 518 can then be used to drive joint sprocket gear 504 using the second drive sprocket gear 516 and actuate the knee joint 104R. The gear ratios for the various components described above can be selected based on a needed amount of torque for a joint, power constraints, and space constraints.

Each stage of the chain drive transmission can include tensioners, which can remove slack from a chain and mitigate shock loading. Such tensioners can be adjustable or spring loaded. For example, as shown in FIG. 5A, spring loaded tensioners 508 and 510 are shown for second chain 518. Similarly, tensioners 509 and 511 can also be provided for first chain 512 (if present).

In addition, a brake can be provided for motor 502. For example, as shown in FIG. 5, a solenoid brake 520 is provided which engages a brake pad 522 against the rotor 524 of the motor 502 in one state, and disengages the brake pad 522 in another state. However, the various embodiments are not limited to this particular brake arrangement and any other methods for providing a brake for motor 502 can be used without limitation.

The configuration illustrated in FIG. 5A has been discussed above with respect to an arrangement of sprocket gears and chains. However, the various embodiments are not limited in this regard. That is, any other arrangement of gears, with or without chains, and providing a reduced profile can be used. Further, the various embodiments are not limited to an arrangement of gears and/or chains For example, in some configurations, a belt and pulley arrangement could be used in place of the chain and sprocket arrangement. Further, a friction drive arrangement can also be used. Also, any combination of the arrangements discussed above can be used as well. Additionally, different joints can employ different arrangements.

In the various embodiments, a motor for each of joints 102R, 102L, 104R, 104L can be configured to provide a baseline amount of continuous torque and a higher amount of torque for shorter periods of time. For example, in one configuration, at least 10 Nm of continuous torque and at least 25 Nm of torque for shorter (i.e., 2-sec) durations are provided. In another example, up to 12 Nm of continuous torque and 40 Nm of torque for shorter (i.e., 2-sec) durations. As a safety measure, both knee joints 104R and 104L can include normally locked brakes, as discussed above, in order to preclude knee buckling in the event of a power failure.

It is worth noting that an exoskeleton in accordance with the various embodiments does not contain foot or ankle components. However, an exoskeleton in accordance with the various embodiments can be configured to be used in conjunction with a standard ankle foot exoskeleton (AFO) 115 to provide stability for the ankle and/or to preclude foot drop during the swing phase of gait.

In the exoskeleton 100, control of the various joints is provided using a pair of embedded control systems 116R and 116L embedded in one of thigh segments 108R and 108L, respectively. The embedded control systems 116R and 116L can be used to define a distributed embedded system (DES) to provide cooperative operation between thigh segments 108R and 108L. The embedded control systems 116R and 116L are shown in FIGS. 3 and 4 using dashed lines to indicate they are concealed by other features in these figures.

A functional diagram of an exemplary DES 600 formed using the embedded control systems 116R and 116L is given in FIG. 6. The DES 600 is powered by battery 111, such as a 29.6 V, 3.9 A·hr lithium polymer battery. The DES 600 can include includes a power management module 602, a computation or data processing module 604, electronic signal conditioning and sensor interface module 606, power electronics 608, and communication electronics 610 to interface components within the DES 600 and between the DES 600 and a host computer. To form the DES 600 the embedded control systems 116R and 116L can be communicatively coupled via wired communications links in the hip segment 110 or wireless communications links between the embedded control systems 116R and 116L. The can include any type of wireless communications links. For example, these can include wireless communication links according to any of the IEEE 802.xx standards, Bluetooth™, and any derivations thereof. However, the various embodiments are not limited in this regard and any other types of wireless communication links can be used.

The power management module 602 provides, from the battery 111 can provide signal conditioning and regulation. Additionally, the power management modules For example, the power management module 602 is configured to provide linearly regulated ±12 and +3.3 V, which are used for signal conditioning and computation, and are derived from intermediate ±12.5 and +5 V switching regulators for efficient conversion. In some embodiments, the exoskeleton 100 can include a visual display, controlled by the power management module 602, to indicate a state of the battery. The visual display can be alphanumeric or symbolic (e.g., one or more lights to indicate battery status).

The computation module 604 consists of microcontroller units within each of embedded control systems 116R and 116L. For example, as shown in FIG. 6, the microcontroller units can be s 80 MHz PIC32 microcontrollers, each with 512 kB flash memory and 32 kB RAM, and each of which consume approximately 400 mW of power. These microcontrollers can be programmed. For example, the programming can be performed in C programming language using MPLAB IDE and the MP32 C Compiler (both from Microchip Technology, Inc.). However, the various embodiments are not limited in this regard and any other types of programming methods can be used.

In operation, the computation module 604 (i.e., the two microcontrollers) drive the motors associated with each of joints 102R, 102L, 104R, and 104L using servodrivers or servoamplifiers in the power electronics 608, such as four-quadrant switching servoamplifiers or pulse-width-modulated (PWM) power transistor drivers. The computation module 604 also drives the knee brakes via pulse-width-modulated (PWM) power transistors in the power electronics 608.

The computation module 604 is configured in the various embodiments to drive the motors associated with each of joints 102R, 102L, 104R, and 104L based, at least in part, on sensor data regarding the state of the exoskeleton 100, as further discussed below. Accordingly, the sensor interface module 606 can be configured to provide and/or provide communications with sensors dispose in exoskeleton 100. In some embodiments, all of the sensors can be disposed within one of thigh segments 108R and 108L. For example, these sensors can be embedded within each of embedded control systems 116R and 116L. In one configuration of exoskeleton 100, physical sensing consists of Hall-effect-based angle and angular velocity sensing in each hip joint 104R, 104L and each knee joint 102R, 102L, and 3-axis accelerometers and single-axis gyroscopes disposed elsewhere in each of thigh segments 108R and 108L.

Although the description above describes a symmetric arrangement of components in for each of embedded control systems 116R and 116L, the various embodiments are not limited in this regard. In other embodiments, one or more of the module described above may be located within one of embedded control systems 116R and 116L.

In some embodiments, the exoskeleton 100 can be configured to operate cooperatively with sensors embedded in the stability aid 103. The DES can be configured to communicate with such sensors via wireline or wireless communications links, as described above.

EXAMPLES

The examples shown here are not intended to limit the various embodiments. Rather they are presented solely for illustrative purposes.

Figure 7:
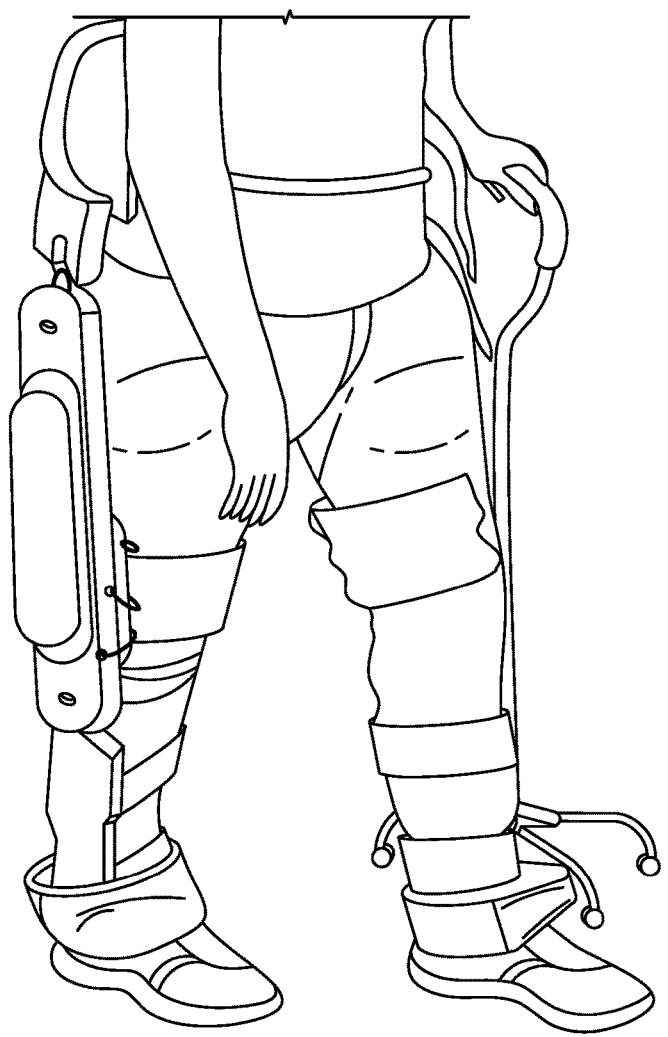
FIG. 7 illustrates a user with an exoskeleton configured in accordance with the various embodiments.

In order to provide a preliminary validation of the control methodology described above, the control approach was implemented on the exoskeleton described above and evaluated on a person in sub-acute stages of stroke recovery. For this preliminary study, assistance was provided for the impaired leg in the swing phase of walking, in an effort to achieve symmetrical stride length. The subject was a 32 year-old female, three months post ischemic stroke, with a right-sided (upper and lower extremity) hemiparesis, able to walk with the aid of a quad cane. An illustration of this individual using the exoskeleton described above operating using the control methodology discussed above is shown in FIG. 7. At the time of testing, the subject was characterized by a FIM gait score of 5 (i.e., supervision required with standby assistance). Note that this is on the upper end of the functional spectrum for the proposed intervention. The subject had expressive and receptive aphasia, although she was not otherwise cognitively impaired.

Figure 8:
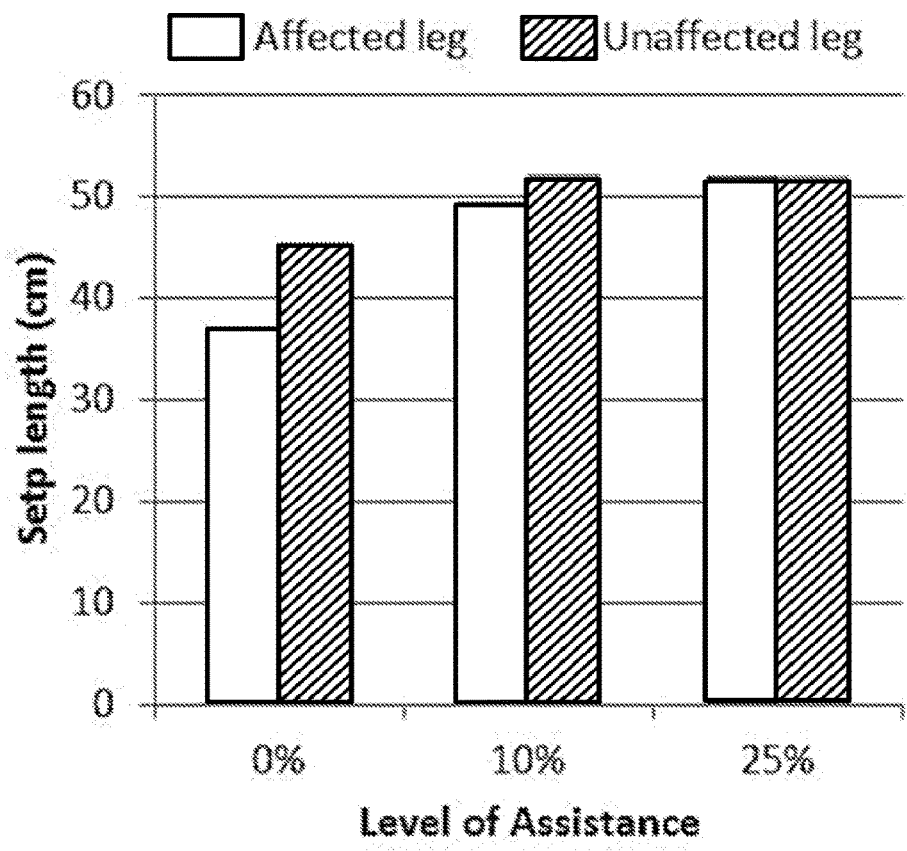
FIG. 8 is a plot of step length for affected and unaffected legs with varying levels of assistance.

Since subject had right-sided hemiparesis, and since compensation was provided for the affected leg in swing only, equation (2) was implemented as the controller, where the amount of affected leg compensation was adjusted $0 \leq r_a < 1$ based on subject need, and the unaffected leg was not given compensation (i.e., $r_u = 0$). As symmetrical stride length was used as a measure of "good stepping," and as such the level of swing phase compensation was incrementally increased until symmetrical step lengths were achieved. FIG. 8 shows the right (affected) and left (unaffected) step lengths when walking overground with the exoskeleton, with three levels of leg weight assistance in swing: 0%, 10%, and 25% assistance.

As seen in FIG. 8, each increase in leg weight assistance results in a corresponding increase in step length on the affected side. Interestingly, although the exoskeleton provided no assistance to the unaffected leg, the increased step length on the affected side had a corresponding effect of increasing the step length on the unaffected side. In the preliminary experiments, the level of affected side swing phase assistance was increased until the right and left side step lengths were equal, as shown in FIG. 8, which occurred at a level of assistance of 25%.

Figure 9A:
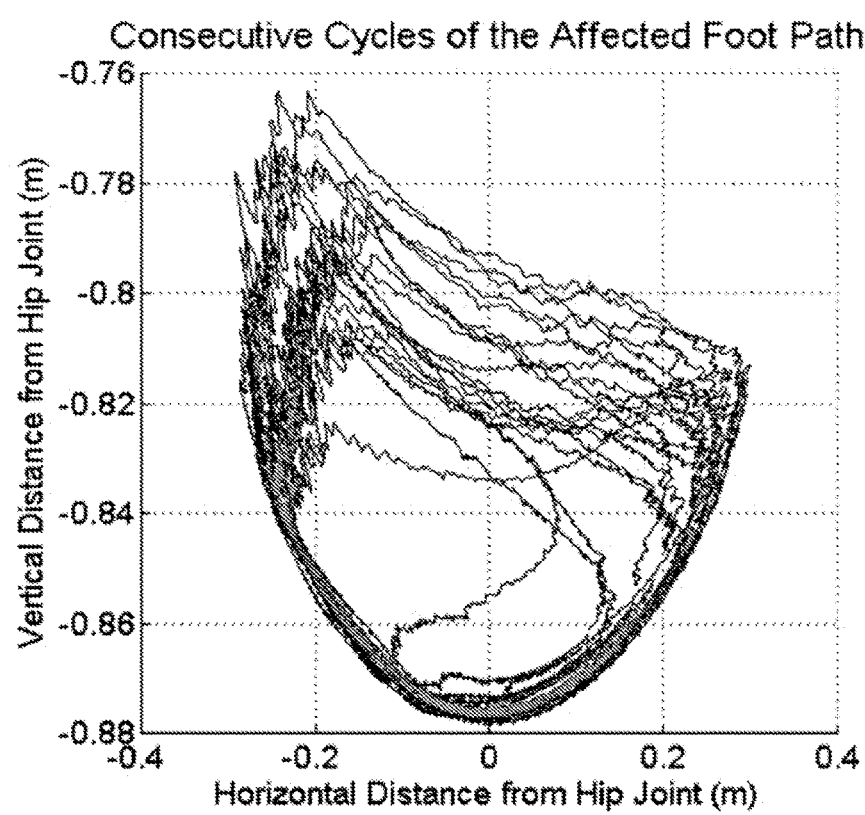
FIG. 9A is a plot of foot path for various levels of assistance.
Figure 9B:
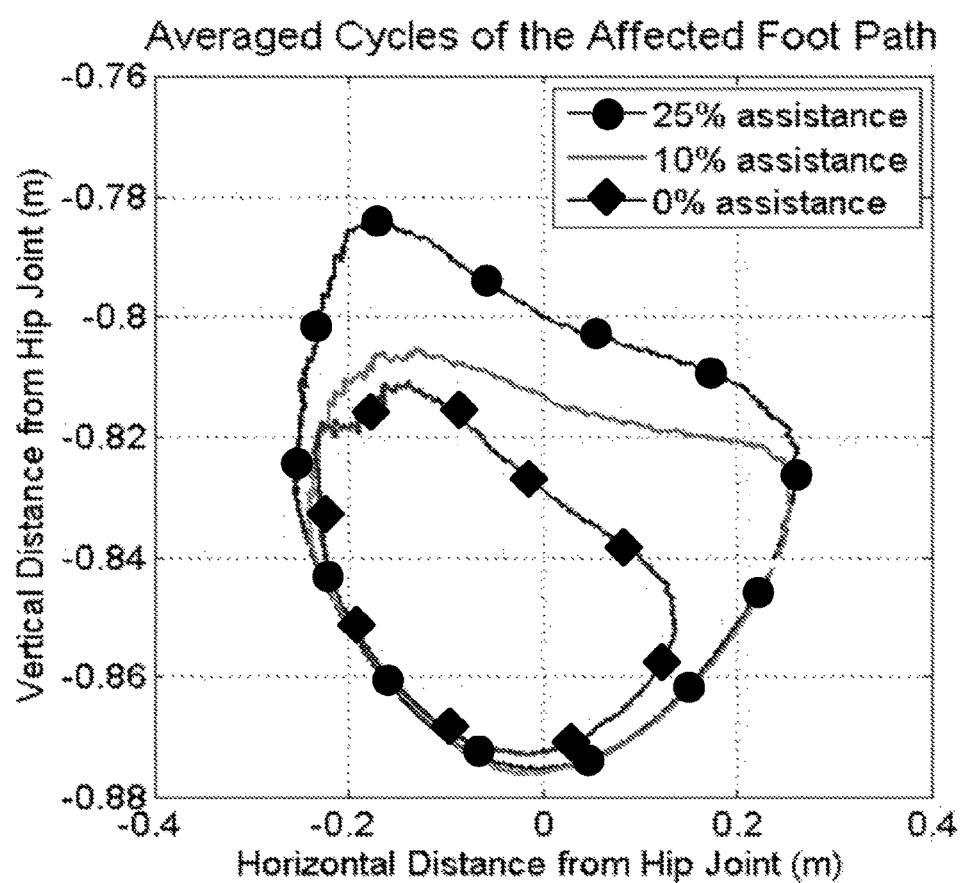
FIG. 9B is a plot of the average foot path for various levels of assistance for the data in FIG. 9A.

In addition to increasing step length and gait symmetry, the increased assistance additionally increased the step height of the affected leg, as shown in FIGS. 9A and 9B. Specifically, FIG. 9A shows the foot paths on the right leg (relative to the subject's hip joint) for several steps of walking at the three levels of exoskeleton assistance, while FIG. 9B shows the same foot paths with each level of assistance averaged together. As seen in FIG. 9B, increased assistance (i.e., effectively making the limb lighter in swing phase) results in both an increase in step length and step height (i.e., ground clearance). Specifically, a level of 25% limb weight assistance corresponds to a ~40% increase in step length, and a ~50% increase in step height, relative to movement without assistance.

Figure 10A:
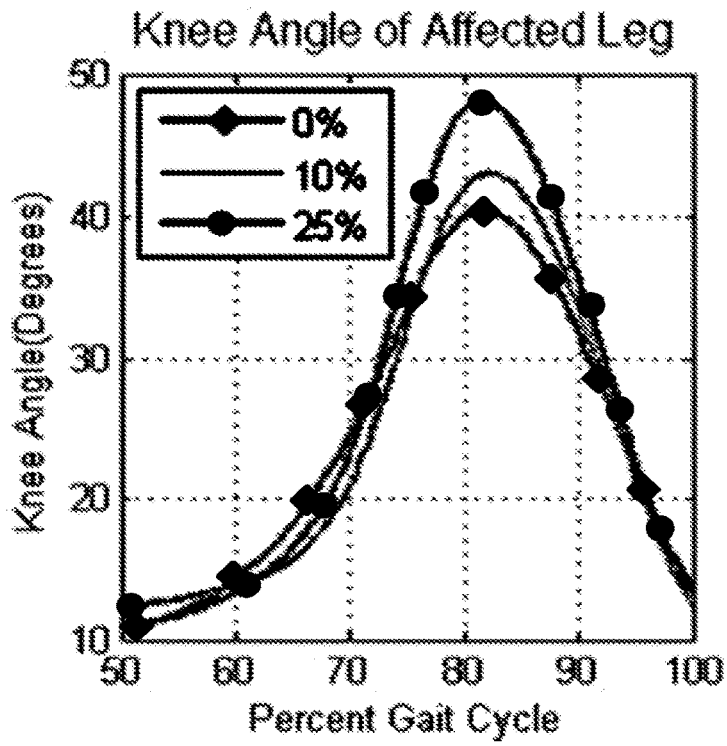
FIG. 10A is a plot of knee angle as a function of percent gait cycle for various levels of assistance.
Figure 10B:
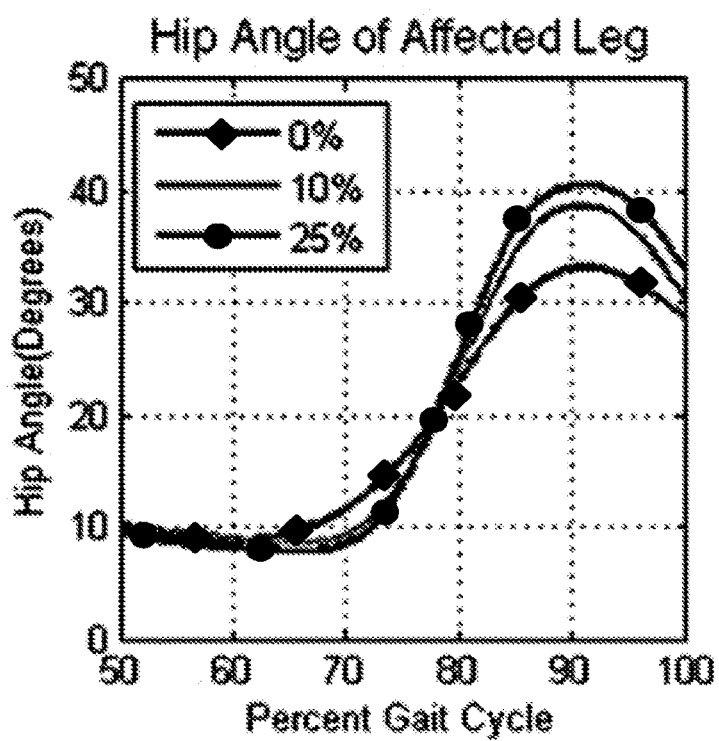
FIG. 10B is a plot of hip angle as a function of percent gait cycle for various levels of assistance.

Finally, as can be seen in FIGS. 10A and 10B, these increases result from increases in flexion at both the hip and knee joints. FIGS. 10 and 10B show plots of knee and hip angle, respectively, as a function of percent of gait cycle, for 0%, 10%, and 25% assistance. As shown in these figures, as the amount of assistance is increased, a greater range of flexion is observed in both the knee and hip joint. That is, the effect is not localized in one joint. Specifically, a level of 25% limb weight assistance corresponds to a ~40% increase in hip flexion range and ~30% increase in knee flexion range relative to movement without assistance.

Other aspects of the present invention are described in the documents attached hereto as Appendix A and Appendix B, the contents of which are hereby incorporated by reference in their entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for the control of an exoskeleton comprising a plurality of segments and one or more powered joints associated with lower limbs of a user, the method comprising:
   obtaining a configuration of a body of the user associated with the exoskeleton with respect to an inertia reference frame and an angular velocity of each of the powered joints;
   estimating an effect of gravity on the lower limbs of the user based on the configuration;
   computing a first control torque for each of the powered joints that at least partially reduces the effect of gravity on an associated one of the lower limbs of the user based on the configuration;
   calculating a gravitational energy gradient for each of the powered joints based on a product of the respective angular velocity and the respective first control torque;
   attenuating the first control torque for each of the powered joints by an attenuation amount selected according to a sign of the respective gravitational energy gradient to yield a second control torque for each of the powered joints; and
   applying a final control torque via each of the powered joints, the final control torque based, at least in part, on the respective second control torque,
   wherein the attenuation amount is zero when the sign is positive, and wherein the attenuation amount is equal to the respective first control torque when the sign is negative.

2. The method of claim 1, further comprising:
   computing a third control torque for each of the powered joints that substantially compensates an effect of gravity on the exoskeleton, and
   wherein the final control torque for each of the powered joints is further based on a sum of the respective second control torque and the respective third control torque.

3. The method of claim 1, wherein the estimating of the configuration comprises utilizing at least one of a gyroscope or an accelerometer to determine an orientation of the plurality of segments relative to the inertia reference frame.

4. The method of claim 3, wherein the estimating of the configuration further comprises sensing joint angles between the segments of the exoskeleton.

5. The method of claim 3 or 4, wherein the estimating of the configuration further comprises:
   determining whether each one of the powered joints is associated with a portion of the exoskeleton corresponding to swing leg or a support leg of the lower limbs of the user,
   in response to determining that the one of the powered joints is associated with the swing leg, computing the first control torque for the one of the powered joints to at least partially compensate for the weight of the swing leg relative to a hip of the user, and
   in response to ascertaining that the one of the powered joints is associated with the support leg, computing the first control torque for the one of the powered joints to at least partially compensate for the weight of the body.

6. The method of claim 5, wherein the powered joints are associated with each of the lower limbs of the user, and wherein the computing further comprises calculating the first control torque for each of the powered joints to provide different amounts of partial gravity compensation for each of the lower limbs.

7. The method of claim 5, wherein the computing further comprises selecting the first control torque for one of the lower limbs to provide zero gravity compensation.

8. The method of claim 5, further comprising determining whether the lower limbs are in a single-support phase or a double-support phase based on the configuration, and adjusting an amount of compensation provided by the first control torque for the one of the powered joints differently for each of the single-support phase and the double-support phase.

9. The method of claim 8, further comprising detecting a transition of the lower limbs between the single-support phase and the double-support phase based on measurements from at least one of a load sensor, a gyroscope, or an accelerometer associated with the exoskeleton.

10. The method of claim 9, wherein the transition from the single-support phase and the double-support phase is detected when the measurements indicate a substantial acceleration in the swing leg along a direction of ground impact.

11. The method of claim 9, wherein the transition from the single-support phase and the double-support phase is detected when the measurements indicate a change in a direction of an angular velocity of a shank segment of the swing leg.

12. The method of claim 8, further comprising detecting a transition of the lower limbs between the single-support phase and the double-support phase based on a change in at least one of a direction or a magnitude of an angular velocity of at least one segment of the exoskeleton associated with the swing leg.

13. The method of claim 8, where an amount of compensation during the single-support phase is determined based on a measured movement of the lower limbs.

14. The method of claim 13, where the amount of compensation for a first leg of the lower limbs is based, at least in part, on the measured movement of a second leg of the lower limbs.

15. The method of claim 13, where the amount of compensation is based on the difference between the measured movement of a first leg of the lower limbs and the measurement movement of a second leg of the lower limbs.

16. The method of claim 1, further comprising adjusting an amount of damping for at least one of powered joints.

17. A non-transitory computer-readable medium having stored thereon a computer program executable on a computing device, the computer program comprising a plurality of code sections for performing the method of claim 1.

18. A control system for controlling an exoskeleton comprising one or more powered joints associated with lower limbs of a user and a plurality of sensors associated with the lower limbs, the control system comprising:
  a sensor interface for receiving sensor signals from the plurality of sensors;
  a power interface for transmitting control signals to the at least one powered joint;
  a processor communicatively coupled to the sensor interface and the power interface; and
  a computer-readable medium having stored thereon a computer program executable on the processor, the computer program comprising a plurality of code sections for:
    obtaining a configuration of a body of the user associated with the exoskeleton with respect to an inertia reference frame and an angular velocity of each of the powered joints based on the sensor signals at the sensor interface,
    estimating an effect of gravity on the lower limbs of the user based on the configuration,
    computing a first control torque for each of the powered joints that at least partially reduces an effect of gravity on an associated one of the lower limbs of the user based on the configuration;
    calculating a gravitational energy gradient for each of the powered joints based on a product of the respective angular velocity and the respective first control torque,
    attenuating the first control torque for each of the powered joints by an attenuation amount selected according to a sign of the respective gravitational energy gradient to yield a second control torque for each of the powered joints,
    computing a final control torque for each of the powered joints, the final control torque based, at least in part, on the respective second control torque, and
    configuring the control signals at the power interface to cause the final control torque to be applied at the at least one powered joint,
    wherein the attenuation amount is zero when the sign is positive, and wherein the attenuation amount is equal to the respective first control torque when the sign is negative.

19. The control system of claim 18, wherein the computer program further comprises code sections for:
  computing a third control torque for each of the powered joints that substantially compensates an effect of gravity on the exoskeleton, and
  wherein the final control torque for each of the powered joints is further based on a sum of the respective second control torque and the respective third control torque.

* * * * *

UNITED STATES PATENT AND TRADEMARK OFFICE
CERTIFICATE OF CORRECTION

PATENT NO. : 9,566,705 B2
APPLICATION NO. : 14/408094
DATED : February 14, 2017
INVENTOR(S) : Goldfarb et al.

Page 1 of 1

It is certified that error appears in the above-identified patent and that said Letters Patent is hereby corrected as shown below:

In the Specification

In Column 1, at Line 14, after the section entitled CROSS-REFERENCE TO RELATED APPLICATIONS, insert the following heading and paragraph:
--GOVERNMENT SUPPORT
This invention was made with government support under grant number HD059832 awarded by the National Institutes of Health. The government has certain rights in the invention.--

Signed and Sealed this
Twenty-sixth Day of November, 2019

Andrei Iancu
*Director of the United States Patent and Trademark Office*